US008906655B2

(12) United States Patent
Barker et al.

(10) Patent No.: US 8,906,655 B2
(45) Date of Patent: Dec. 9, 2014

(54) ALCOHOL PRODUCTION PROCESS

(71) Applicant: LanzaTech New Zealand Limited, Roselle, IL (US)

(72) Inventors: Will David Barker, Auckland (NZ); Bjorn Daniel Heijstra, Auckland (NZ); Wing Chuen Chan, Auckland (NZ); Christophe Daniel Mihalcea, Auckland (NZ); Loan Phuong Tran, Auckland (NZ); Christophe Collet, Auckland (NZ); Jason Carl Bromley, Auckland (NZ); Bakir Al-Sinawi, Auckland (NZ)

(73) Assignee: Lanzatech New Zealand Limited, Auckland (NZ)

( * ) Notice: Subject to any disclaimer, the term of this patent is extended or adjusted under 35 U.S.C. 154(b) by 0 days.

(21) Appl. No.: 13/872,646

(22) Filed: Apr. 29, 2013

(65) Prior Publication Data

US 2013/0252230 A1 Sep. 26, 2013

Related U.S. Application Data

(63) Continuation of application No. 13/060,862, filed as application No. PCT/NZ2010/000136 on Jul. 2, 2010, now abandoned.

(60) Provisional application No. 61/222,920, filed on Jul. 2, 2009, provisional application No. 61/226,341, filed on Jul. 17, 2009.

(51) Int. Cl.
C12P 7/06 (2006.01)
C12Q 3/00 (2006.01)
C12P 7/54 (2006.01)
C12M 1/34 (2006.01)
C12M 1/36 (2006.01)

(52) U.S. Cl.
CPC . C12Q 3/00 (2013.01); C12P 7/065 (2013.01); C12P 7/54 (2013.01); C12M 41/34 (2013.01); C12M 41/48 (2013.01); Y02E 50/17 (2013.01)
USPC ......................................................... 435/161

(58) Field of Classification Search
None
See application file for complete search history.

(56) References Cited

U.S. PATENT DOCUMENTS

| 5,173,429 | A | 12/1992 | Gaddy et al. |
| 5,593,886 | A | 1/1997 | Gaddy |
| 5,807,722 | A | 9/1998 | Gaddy |
| 5,821,111 | A | 10/1998 | Grady et al. |
| 6,136,577 | A | 10/2000 | Gaddy |
| 6,340,581 | B1 | 1/2002 | Gaddy |
| 6,368,819 | B1 | 4/2002 | Gaddy et al. |
| 6,753,170 | B2 | 6/2004 | Gaddy et al. |
| RE39,175 | E | 7/2006 | Gaddy et al. |
| 7,196,218 | B2 | 3/2007 | Gaddy et al. |
| 7,285,402 | B2 | 10/2007 | Gaddy et al. |
| 2003/0211585 | A1 | 11/2003 | Gaddy et al. |
| 2007/0275447 | A1 | 11/2007 | Lewis et al. |

FOREIGN PATENT DOCUMENTS

| WO | WO02/08438 | 1/2002 |
| WO | WO2007/117157 | 10/2007 |
| WO | 2008028055 | 3/2008 |
| WO | 2008154301 | 12/2008 |
| WO | 2009020747 | 2/2009 |
| WO | 2009022925 | 2/2009 |
| WO | WO 2009/058028 | 5/2009 |
| WO | 2009113878 | 9/2009 |
| WO | 2010064932 | 6/2010 |
| WO | 2010064933 | 6/2010 |
| Wo | 2010093262 | 8/2010 |
| WO | 2010098679 | 9/2010 |

OTHER PUBLICATIONS

Phillips, J.R., et al. "Synthesis Gas as Substrate for the Biological Production of Fuels and Chemicals" Applied Biochemistry and Biotechnology, 1994 45/46 pp. 145-157.
Abrini J. et al. "Clostridium autoethanogenum, sp. nov., an Anaerobic Bacterium that Produces Ethanol from Carbon Monoxide", Archives of Microbiology. 1994 vol. 161, pp. 345-351.
PCT International Search Report dated Mar. 21, 2012.
EP Search Opinion dated Dec. 19, 2013.

Primary Examiner — Allison Fox
Assistant Examiner — Yvonne Pyla
(74) Attorney, Agent, or Firm — Frank S. Molinaro

(57) ABSTRACT

The invention relates to a process for optimizing the production of ethanol by microbial fermentation, particularly microbial fermentation of substrates comprising CO. The process involves monitoring the hydrogen production by the microorganism, determining an optimum hydrogen production and adjusting the substrate supply rate in response to a change in the hydrogen production thereby keeping the hydrogen production within a desired range.

7 Claims, 8 Drawing Sheets

ALCOHOL PRODUCTION PROCESS

CROSS REFERENCE TO RELATED APPLICATION

This application is a continuation of copending U.S. non-provisional application Ser. No. 13/060,862 filed on May 17, 2011 which in turn is a national phase (35 U.S.C. §371) of international application No. PCT/NZ2010/000136 filed on Feb. 7, 2010 which claims the priority of U.S. provisional application 61/222,920 filed on Feb. 7, 2009 and U.S. provisional application 61/226,341 filed on Jul. 17, 2009. All of the above applications are incorporated by reference in their entirety.

FIELD OF THE INVENTION

This invention relates generally to a process for optimising the production of ethanol by microbial fermentation, particularly microbial fermentation of substrates comprising CO. The amount of hydrogen produced during the process is monitored and an optimum hydrogen production is determined. The substrate supply rate is adjusted in response to a change in the hydrogen production.

BACKGROUND OF THE INVENTION

Ethanol is rapidly becoming a major hydrogen-rich liquid transport fuel around the world. Worldwide consumption of ethanol in 2005 was an estimated 12.2 billion gallons. The global market for the fuel ethanol industry has also been predicted to continue to grow sharply in future, due to an increased interest in ethanol in Europe, Japan, the USA and several developing nations.

For example, in the USA, ethanol is used to produce E10, a 10% mixture of ethanol in gasoline. In E10 blends, the ethanol component acts as an oxygenating agent, improving the efficiency of combustion and reducing the production of air pollutants. In Brazil, ethanol satisfies approximately 30% of the transport fuel demand, as both an oxygenating agent blended in gasoline, and as a pure fuel in its own right. Also, in Europe, environmental concerns surrounding the consequences of Green House Gas (GHG) emissions have been the stimulus for the European Union (EU) to set member nations a mandated target for the consumption of sustainable transport fuels such as biomass derived ethanol.

The vast majority of fuel ethanol is produced via traditional yeast-based fermentation processes that use crop derived carbohydrates, such as sucrose extracted from sugarcane or starch extracted from grain crops, as the main carbon source. However, the cost of these carbohydrate feed stocks is influenced by their value as human food or animal feed, and the cultivation of starch or sucrose-producing crops for ethanol production is not economically sustainable in all geographies. Therefore, it is of interest to develop technologies to convert lower cost and/or more abundant carbon resources into fuel ethanol.

CO is a major, energy-rich by-product of the incomplete combustion of organic materials such as coal or oil and oil derived products. Other industrial processes also result in the production of carbon monoxide. The steel industry in Australia is reported to produce and release into the atmosphere over 500,000 tonnes of CO annually.

Catalytic processes may be used to convert gases consisting primarily of CO and/or CO and hydrogen ($H_2$) into a variety of fuels and chemicals. Micro-organisms may also be used to convert these gases into fuels and chemicals. These biological processes, although generally slower than chemical reactions, have several advantages over catalytic processes, including higher specificity, higher yields, lower energy costs and greater resistance to poisoning.

The ability of micro-organisms to grow on CO as a sole carbon source was first discovered in 1903. This was later determined to be a property of organisms that use the acetyl coenzyme A (acetyl CoA) biochemical pathway of autotrophic growth (also known as the Woods-Ljungdahl pathway and the carbon monoxide dehydrogenase/acetyl CoA synthase (CODH/ACS) pathway). A large number of anaerobic organisms including carboxydotrophic, photosynthetic, methanogenic and acetogenic organisms have been shown to metabolize CO to various end products, namely $CO_2$, $H_2$, methane, n-butanol, acetate and ethanol. While using CO as the sole carbon source, all such organisms produce at least two of these end products.

Anaerobic bacteria, such as those from the genus *Clostridium*, have been demonstrated to produce ethanol from CO, $CO_2$ and $H_2$ via the acetyl CoA biochemical pathway. For example, various strains of *Clostridium ljungdahlii* that produce ethanol from gases are described in WO 00/68407, EP 117309, U.S. Pat. Nos. 5,173,429, 5,593,886, and 6,368,819, WO 98/00558 and WO 02/08438. The bacterium *Clostridium autoethanogenum* sp is also known to produce ethanol from gases (Abrini et al., Archives of Microbiology 161, pp 345-351 (1994)).

However, ethanol production by micro-organisms by fermentation of gases is typically associated with co-production of acetate and/or acetic acid. As some of the available carbon is converted into acetate/acetic acid rather than ethanol, the efficiency of production of ethanol using such fermentation processes may be less than desirable. Also, unless the acetate/acetic acid by-product can be used for some other purpose, it may pose a waste disposal problem. Acetate/acetic acid is converted to methane by micro-organisms and therefore has the potential to contribute to GHG emissions.

WO2007/117157, WO2008/115080 and WO2009/022925, the disclosure of which are incorporated herein by reference, describe processes that produce alcohols, particularly ethanol, by anaerobic fermentation of gases containing carbon monoxide. WO2007/117157, describes a process that produces alcohols, particularly ethanol, by anaerobic fermentation of gases containing carbon monoxide. Acetate produced as a by-product of the fermentation process is converted into hydrogen gas and carbon dioxide gas, either or both of which may be used in the anaerobic fermentation process. WO2008/115080, describes a process for the production of alcohol(s) in multiple fermentation stages. By-products produced as a result of anaerobic fermentation of gas(es) in a first bioreactor can be used to produce products in a second bioreactor. Furthermore, by-products of the second fermentation stage can be recycled to the first bioreactor to produce products. WO2009/022925 discloses the effect of pH and ORP in the conversion of substrates comprising CO to products such as acids and alcohols by fermentation.

Microbes capable of growing on CO-containing gases are known to do so at a slower rate than is traditionally associated with microbes grown on sugars. From a commercial perspective, in a fermentation process the time required for a microbial population to grow to a sufficiently high cell density to allow an economically viable level of product to be synthesised, is a key operating cost affecting the profitability of the process. Technologies that act to enhance culture growth rates and/or productivities and therefore reduce the time required to reach desired cell densities and/or desired product levels and may serve to improve the commercial viability of the overall process.

In fermentation processes dedicated to the production of alcohols from gas feedstocks, ensuring that the appropriate conditions for microbial growth and/or alcohol production, can be critical to maintaining optimal microbial growth and/or alcohol productivities. For example, it is recognised that providing a substrate to a microbial culture at or toward an optimum level or range can result in optimal microbial growth and/or desired metabolite production as described in PCT/NZ2010/000009 which is fully incorporate herein by reference. For example, if too little substrate is provided, microbial growth slows and the fermentation product(s) are predominantly acid(s) such as acetate, whereas too much substrate can lead to poor microbial growth and/or cell death.

Due to the low solubility of CO and the lack of accurate means for measuring dissolved, it is difficult to determine how much CO is available to a microbial culture at a given time point under particular conditions. Thus, it can be difficult to determine an optimum level of CO to provide to a microbial culture for conversion into products at any particular time.

It is an object of the present invention to provide a process that goes at least some way towards overcoming the above disadvantages, or at least to provide the public with a useful choice.

SUMMARY OF THE INVENTION

In a first broad aspect of the invention, there is provided a method of optimising supply of a substrate comprising CO to a bioreactor, wherein the substrate is fermented to produce products including one or more alcohol(s) and/or acid(s) by a culture of one or more carboxydotrophic microorganisms, the method including determining acid levels in the bioreactor at a first time point and a second time point, wherein a change in acid level between the first and second time points results in a change in substrate supply.

In particular embodiments, an increase in acid level between the first and second time points results in an increase in substrate supply.

In particular embodiments, a decrease in acid level between the first and second time points results in a decrease in substrate supply.

In a second broad aspect of the invention, there is provided a method of increasing efficiency of fermentation of a substrate comprising CO in a bioreactor, by a culture of one or more carboxydotrophic microorganisms, to produce products including acid(s) and/or alcohol(s), wherein the substrate is provided such that acid levels are maintained between predetermined threshold concentrations in the bioreactor.

In particular embodiments, the substrate supply is automatically controlled in response to changes in acid levels.

In particular embodiments, acid levels are maintained between predetermined threshold concentrations of 1-10 g/L fermentation broth. In particular embodiments, acid levels are maintained between predetermined threshold concentrations of 2-8 g/L fermentation broth. In particular embodiments, acid levels are determined by measuring pH of the culture.

In particular embodiments, the fermentation is continuous.

In a third broad aspect of the invention, there is provided a method of determining an optimum substrate supply level and/or range, the method including providing a substrate to a culture of one or more carboxydotrophic microorganisms in a bioreactor, at or substantially toward a level such that a desired ratio of alcohol:acid products is produced by fermentation of a substrate comprising CO.

In particular embodiments of the preceding aspects, the acid is acetate. In particular embodiments, the alcohol is ethanol.

In a fourth broad aspect of the invention, there is provided a method of improving overall efficiency of microbial fermentation of a substrate to produce products, the method comprising providing the substrate to a microbial culture substantially towards an optimum level, at an optimum level or within an optimum range.

In particular embodiments, the substrate comprises CO.

In particular embodiments, the products are acid(s) and/or alcohol(s). In particular embodiments of the invention, alcohol (particularly ethanol) is produced without concomitant production of acid (particularly acetate).

In particular embodiments, the method includes providing the substrate such that pH of a fermentation media remains substantially constant or within a predetermined range. In particular embodiments, the substrate is provided such that there is substantially no net change in acid(s) concentration during fermentation.

In particular embodiments, the substrate is provided such that pH is maintained within a desirable range. In particular embodiments, the desirable range is ±0.5 units of the optimum operating pH. Typically, the substrate is provided such that pH is maintained between 5-6; or between 5.1-5.9; or within 5.2-5.8; or between 5.3-5.7; or between 5.4-5.6; or substantially at 5.5.

In a fifth broad aspect, there is provided a method of improving overall efficiency of microbial fermentation of a substrate to produce products, the method including monitoring pH and controlling substrate supply based on pH changes. In particular embodiments, the substrate comprises CO.

In particular embodiments, provision of the substrate is controlled such that pH remains substantially constant or within a predetermined range or changes with a predetermined rate of change.

In particular embodiments, the method includes increasing substrate supply in response to a decrease in pH. Additionally or alternatively, the method includes decreasing the substrate supply in response to an increase in pH.

In particular embodiments of the invention, the method includes monitoring metabolite concentration in a fermentation broth by known analytical methods.

In a sixth broad aspect of the invention, there is provided a method of improving overall efficiency of microbial fermentation of a substrate to produce products, the method comprising providing the substrate to a microbial culture substantially towards an optimum level, at an optimum level or within an optimum range.

In particular embodiments, the substrate comprises CO.

In particular embodiments, the products are acid(s) and/or alcohol(s). In particular embodiments, products are produced such that a desirable product ratio of at least 1:1; or at least 1:2; or at least 1:3; or at least 1:4; or at least 1:5; or at least 1:10; or at least 1:20; acid:alcohol is produced by the culture. In particular embodiments of the invention, alcohol (particularly ethanol) is produced without concomitant production of acid (particularly acetate).

In particular embodiments, the method includes providing the substrate such that hydrogen is produced by the microbial culture. In particular embodiments, the substrate is provided such that hydrogen is produced at a level of at least 0.5 mol %; or at least 1.0 mol %; or at least 1.5 mol %; or at least 2.0 mol % of the substrate consumed by the microbial culture. Additionally or alternatively, the substrate is provided such that specific CO uptake by the microbial culture is maintained between 0.6-1.5 mmol CO consumed per gram of biomass per minute (mmol/g/min). In particular embodiments, wherein the substrate comprises CO, as the substrate availability increases above an optimal amount (or above an optimum range), excess CO inhibits hydrogenase enzyme(s), thus substantially preventing H2 production. As hydrogenase enzyme(s) are inhibited, the microbe cannot relieve itself of excess reducing power, thus leading to culture problems such as growth inhibition and/or microbial death.

In a seventh broad aspect, there is provided a method of improving overall efficiency of microbial fermentation of a substrate to produce products, the method including monitoring hydrogen produced by a microbial culture and controlling substrate supply based on hydrogen production.

In particular embodiments, the substrate comprises CO.

In particular embodiments of the invention, provision of the substrate is controlled such that hydrogen produced by the microbial culture at a level of at least 0.5 mol %; or at least 1.0 mol %; or at least 1.5 mol %; or at least 2.0 mol % of the substrate consumed by the culture.

In particular embodiments, the substrate supply is increased such that hydrogen production is maintained at a level of at least 0.5 mol %; or at least 1.0 mol %; or at least 1.5 mol %; or at least 2.0 mol % of the substrate consumed by the microbial culture. Additionally or alternatively, substrate supply can be decreased or maintained substantially constant, such that hydrogen production is maintained at a level at least 0.5 mol %; or at least 1.0 mol %; or at least 1.5 mol %; or at least 2.0 mol % of the substrate consumed by the microbial culture.

In an eighth aspect, there is provided a method of improving overall efficiency of microbial fermentation of a substrate to produce products, the method comprising providing the substrate comprising CO, to a microbial culture such that the specific uptake of the microbial culture is substantially maintained between 0.6-1.5 mmol CO consumed per gram of biomass per minute (mmol/g/min). In particular embodiments, the substrate comprising CO is provided such that specific uptake is substantially maintained between 0.8-1.2 mmol/g/min.

In particular embodiments of the various aspects, the substrate comprising CO is gaseous. In particular embodiments, the gaseous substrate comprises a gas obtained as a by-product of an industrial process. In certain embodiments, the industrial process is selected from the group consisting of ferrous metal products manufacturing, non-ferrous products manufacturing, petroleum refining processes, gasification of biomass, gasification of coal, electric power production, carbon black production, ammonia production, methanol production and coke manufacturing. Substrates having lower concentrations of CO, such as 6%, may also be appropriate, particularly when $H_2$ and $CO_2$ are also present.

In certain embodiments of the various aspects, the CO-containing substrate will typically contain a major proportion of CO, such as at least about 20% to about 100% CO by volume, from 40% to 95% CO by volume, from 40% to 60% CO by volume, and from 45% to 55% CO by volume. In particular embodiments, the substrate comprises about 25%, or about 30%, or about 35%, or about 40%, or about 45%, or about 50% CO, or about 55% CO, or about 60% CO by volume.

In particular embodiments of the various aspects, the alcohol produced by the fermentation process is ethanol. The fermentation reaction may also produce acetate.

In particular embodiments of the various aspects, the fermentation reaction is carried out by one of more strains of acetogenic bacteria. Preferably, the acetogenic bacterium is selected from *Clostridium*, *Moorella* and *Carboxydothermus*, such as *Clostridium autoethanogenum*, *Clostridium ljungdahlii* and *Morella thermoacetica*. In one embodiment, the acetogenic bacterium is *Clostridium autoethanogenum*.

In a ninth broad aspect of the invention, there is provided a system for microbial fermentation of a substrate to produce products, including a bioreactor configured to conduct a desired fermentation, determining means configured to determine pH of a fermentation broth during the desired fermentation and controlling means adapted to control substrate supply.

In particular embodiments, the system is configured to provide a substrate comprising CO.

In particular embodiments, the controlling means are configured to make one or more adjustments to substrate supply if the pH has deviated from a predetermined value or range.

In particular embodiments, the system includes processing means. In particular embodiments, the processing means are linked to the controlling means, such that substrate supply can be automatically regulated in response to changes in pH. In particular embodiments, the substrate supply is controlled such that increasing amounts of substrate are supplied when pH decreases and/or lesser amounts of substrate are provided when pH increases.

In a tenth broad aspect of the invention, there is provided a system for microbial fermentation of a substrate to produce products, including a bioreactor configured to conduct a desired fermentation, determining means configured to determine an amount of hydrogen produced during the desired fermentation and controlling means adapted to control substrate supply.

In particular embodiments, the system is configured to provide a substrate comprising CO. In certain embodiments, the determining means also determines the amount of substrate consumed during fermentation. The determining means can optionally be linked to a processing means such that a $H2_{produced}/CO_{consumed}$ ratio can be determined.

In particular embodiments, the controlling means are configured to make one or more adjustments to substrate supply if the $H2_{produced}/CO_{consumed}$ ratio has deviated from a predetermined value or range.

In particular embodiments, the processing means are linked to the controlling means, such that substrate supply can be automatically regulated in response to changes in H2 production and/or the $H2_{produced}/CO_{consumed}$ ratio.

In an eleventh broad aspect of the invention, there is provided a system for microbial fermentation to produce products including:
a. a bioreactor configured to conduct fermentation of a substrate comprising CO
b. determining means; and
c. controlling means;
wherein, the controlling means are configured to control supply of a substrate comprising CO in response to the determination made by the determining means.

In particular embodiments, the determining means is configured to determine the amount of one or more acid(s) produced in a fermentation.

In particular embodiments, the determining means is configured to determine the pH of fermentation.

In particular embodiments, the determining means is configured to determine the amount of H2 produced in fermentation.

Although the invention is broadly as defined above, it is not limited thereto and also includes embodiments of which the following description provides examples.

BRIEF DESCRIPTION OF THE DRAWINGS

The invention will now be described in detail with reference to the accompanying Figures in which.

DETAILED DESCRIPTION OF THE INVENTION

Figure 1:
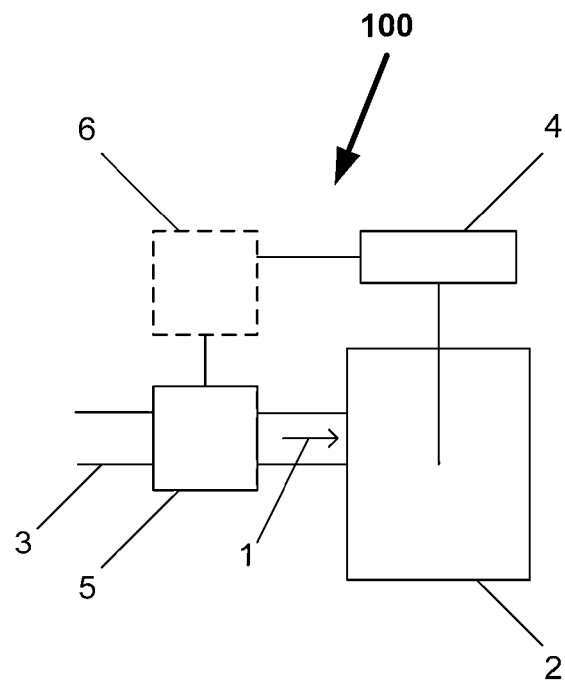
FIG. 1: is a schematic representation according to one embodiment of the invention.

According to particular aspects of the invention, there are provided methods of improving overall efficiency of microbial fermentation of a substrate, the method comprising providing the substrate substantially at an optimum level, towards an optimum level or within an optimum range. In particular embodiments of the invention, the substrate comprises CO and is provided to one or more carboxydotrophic bacteria, such as acetogenic bacteria. Under suitable anaerobic conditions, acetogenic bacteria, such as *Clostridium autoethanogenum, Clostridium ljungdahlii, Clostridium ragsdalei* and *Clostridium carboxydivorans* convert a substrate comprising CO into products including acids and alcohols.

It has been recognised that supplying a substrate, such as a substrate comprising CO, to a microbial culture at or toward an optimum level or range can result in optimal microbial growth and/or desired metabolite production, as described in PCT/NZ2010/000009, which is fully incorporated herein by reference. For example, it is recognised that supplying a substrate comprising CO at or towards an optimum level, to a microbial culture comprising one or more carboxydotrophic microorganisms results in good microbial growth and production of desired products, such as one or more alcohols.

In order to maintain optimal microbial growth and production of desired products, the substrate must be provided to the microbial culture at or toward an optimal level substantially continuously over the course of fermentation. Deviation from the optimum supply can lead to a slowdown in growth, production of less desirable products or in extreme cases, can result in inhibition of microbial growth or microbial death.

Without wishing to be bound by theory, it is considered that at least a portion of a substrate, particularly a substrate comprising CO, is oxidised by a microbial culture to produce energy (reducing equivalents) that may be used in the production of metabolites and/or in cellular growth. Increasing the substrate supply leads to an increase in reducing equivalents available for production of metabolites and/or growth. Typically, in a substrate limited culture, reducing equivalents are used in order for the microbial culture to grow and produce products such as acid(s). However, as substrate supply is increased, a microbe can use the additional substrate to produce additional reducing equivalents, which can be used to reduce product(s) such as acid(s) to desirable products such as alcohol(s). As substrate supply is increased towards an optimum level, the amount of alcohol(s) increases relative to the acid(s), as the microbe uses the increasing amounts of reducing equivalents. Typically, in such embodiments, the microbial culture will grow and produce alcohol(s), such as ethanol.

The substrate supply or level at which a substrate is provided to one or more microorganisms is substantially related to the mass transfer rate of the substrate into an aqueous fermentation broth. Mass transfer of a gas into a liquid is a function of three main variables:

Concentration Driving Force: The partial pressure of a particular gaseous component is substantially proportional to the rate at which that component can be driven into a solution.

Interfacial Surface Area: The larger the interfacial surface area between gas and liquid phases, the higher the opportunity for mass transfer. In particular, the interfacial surface area is typically a function of gas hold-up and bubble size.

Transfer Coefficient: The transfer coefficient of a system is influenced by a variety of factors. However, from a practical perspective, typically the largest influence is the relative velocity between the liquid and the gas phases. Relative velocities (and hence mass transfer) are typically increased by increasing turbulence through agitation or other mixing.

Those skilled in the art will be aware of methods for increasing mass transfer of a substrate into solution. However, by way of example, the substrate supply or level can be increased by one or more of: increasing the rate at which a substrate is provided to a bioreactor, increasing partial pressure of the substrate, or by mechanical means such as increasing the agitation of a stirred tank bioreactor, or increasing the mass transfer characteristics of a particular bioreactor. Many devices and equipment for promotion of mass transfer to microorganisms in fermentation of gaseous substrates are known.

It has been recognised that increasing the amount of substrate available to the microbial culture, for conversion to products, toward an optimum level leads to an increase in the amount of alcohol(s) produced, relative to acid(s). In particular embodiments of the invention, products are produced such that a desirable product ratio of at least 1:1; or at least 1:2; or at least 1:3; or at least 1:4; or at least 1:5; or at least 1:10; or at least 1:20; acid: alcohol is produced by the culture. In particular embodiments, steady state continuous fermentation of a substrate comprising CO will produce products including acetate and/or alcohols. In particular embodiments, at steady state, when the substrate is provided at or toward an optimum level, acetate is maintained at a concentration of less than 10 g/L, or less than 9 g/L, or less than 8 g/L, or less than 7 g/L, or less than 6 g/l, or less than 5 g/L in the fermentation broth.

In other embodiments of the invention, alcohol (particularly ethanol) is produced without concomitant production of acid (particularly acetate). However, over-availability (through oversupply) of substrate can lead to culture problems, such as growth inhibition and/or microbial death.

In accordance with particular aspects, the invention provides methods of optimising microbial fermentation of a substrate, particularly a substrate comprising CO, by controlling the supply of the substrate, such that it is provided at an optimum level, towards an optimum level or within an optimum range to promote culture viability and growth and production of desirable metabolites, such as ethanol. It is recognised that the optimum level (or range) may change over time due to the size of the microbial population. For example, in particular embodiments, a substrate is provided at or toward an optimum level, when the culture produces acid(s), such as acetate, at a specific rate of less than 2 g/g biomass/day, or less than 1.5 g/g/day, or less than 1.2 g/g/day, or less than 1 g/g/day.

Thus, the methods of the invention provide means of optimising substrate supply irrespective of the size of the microbial culture. For example, in batch or fed-batch fermentation, a microbial culture will grow exponentially during the growth phase. As such, the substrate should be supplied in increasing amounts, such that a substantially optimal amount of substrate is continuously provided. Additionally or alternatively, in a continuous culture, the substrate must be provided at or toward an optimum level or range over an extended period to maintain sustainable microbial growth and desired metabolite production. It is recognised small changes in operating conditions such as fresh media supply rate, temperature, pH, ORP, culture viability can result in changes in biomass levels and thus substrate requirements. In accordance with the methods of the invention, substrate can be supplied at or toward an optimum level, irrespective of changes in biomass.

According to particular aspects, the method of optimisation includes monitoring pH of a fermentation media and controlling supply of a substrate based on pH determinations or changes in pH over time. In particular embodiments, a substrate is provided to a microbial culture in fermentation media such that pH of the media changes substantially at or toward a predetermined rate of change or within a predetermined rate of change range. In particular embodiments, the rate of change approaches zero, such that in some embodiments pH of the media is substantially maintained constant or within a pre-determined range. In particular aspects of the invention, during periods of limited substrate supply, acetogenic bacteria produce products including acetic acid. As such, pH of a fermentation media containing a substrate limited acetogenic culture will decrease unless it can be controlled by addition of a base. In accordance with the invention described in WO2009/113878, which is fully incorporated herein by reference, when a substrate comprising CO is oversupplied, acetate will be converted to alcohol and the pH will increase unless it can be controlled by addition of an acid. Thus, under optimal growth and/or alcohol production conditions, acidic metabolites may be produced or consumed by a microbial culture. In particular embodiments, optimal alcohol productivity is associated with the co-production of acid(s) such as acetate. Thus, the production of acidic metabolites, such as acetate will result in a decrease in pH of the fermentation broth over time. In particular embodiments of the invention, products are produced such that a desirable product ratio of at least 1:1; or at least 1:2; or at least 1:3; or at least 1:4; or at least 1:5; or at least 1:10; or at least 1:20; acid:alcohol is produced by the culture and pH will change as a result of acid production by the microbial culture.

It is recognised pH of a fermentation broth may change due to various influences such as consumption or production of one or more acids or bases, or a combination thereof. For example, nitrogen fixation by a microbial culture during microbial growth can result in a decrease in pH. In particular embodiments, carboxydotrophic microorganisms such as *Clostridium autoethanogenum* can uptake nitrogen in the form of $NH_3$ which can result in a decrease in pH of a fermentation broth over time. Other metabolites, such as phosphate and/or lactate may also be produced and/or consumed by the microbial culture, thus affecting the pH of a fermentation broth. It is recognised that acetate is typically a significant product in fermentation by acetogenic bacteria, and typically has the largest influence on the pH.

Accordingly, in particular embodiments, the invention provides a method of providing a substrate at or toward an optimal level or range, the method including maintaining pH change substantially at or toward a predetermined rate of change. In accordance with particular embodiments, a desired rate of change of pH for a given microbial culture can be determined experimentally. For example, a microbial culture can be supplied an optimal amount of substrate for optimal growth and/or desired metabolite production and pH changes monitored. During fermentation acidic and/or basic components may be produced and/or consumed by the microbial culture, resulting in a change in pH over time. This (pre)determined rate of change of pH can then be used to control substrate supply to a microbial culture in subsequent fermentations.

In particular embodiments, an optimally supplied culture of microorganisms grows and produces metabolites including alcohols (such as ethanol) and acids (such as acetate). During steady state production of metabolites, the production of acid(s) will remain substantially constant such that there is a substantially constant rate of change of pH. If pH decreases quicker than the predetermined rate of change, it can be determined that more acid(s) are being produced by the culture and the substrate supply can be increased toward the optimum rate. If the pH decreases slower than the predetermined rate of change, it can be inferred that acid(s) are produced at a slower rate by the culture and the substrate supply can be decreased toward the optimum rate. If the pH increases, it can be inferred that acid(s) are consumed by the culture and the substrate supply can be decreased toward the optimum rate.

In another embodiment, pH change can be counteracted by addition of an acid or a base to maintain a substantially constant pH. In such embodiments, the rate of acid/base added to the fermentation can be used to determine the optimum substrate supply.

In particular embodiments, it has been surprisingly recognised that microbial growth and alcohol production can be optimised by maintaining pH at a predetermined level, or within a predetermined range, by supplying a substrate, particularly a substrate comprising CO, at a desirable level. pH can be maintained at a predetermined level, or within a predetermined range by ensuring there is no net production or consumption of acidic metabolites, such as acetate. In such embodiments, the rate of change of pH is approximately zero. If, during fermentation, the pH starts to decrease it can be inferred that acid(s), such as acetate, is produced by the culture and that the culture is substrate limited. Thus, in accordance with the methods of the invention, the substrate supply should be increased. Conversely, if during fermentation, the pH starts to rise, it can be inferred that there is a net conversion of acid(s), such as acetate, into alcohol(s), such as ethanol, and that the culture is oversupplied with substrate. Thus, in accordance with the methods of the invention, the substrate supply should be decreased.

This control method is of particular importance in a growing microbial culture, as the substrate requirement of the culture will change over time. For example, an optimal level of substrate at one time point may be a limiting amount of substrate at a later time point, if the culture has grown in batch operation. It is considered during exponential growth, the optimum amount of substrate required will also increase substantially exponentially. In continuous operation, even at steady state, the dynamic state of the culture means a substrate supply can be continuously supplied at or towards an optimum level or range in response to small changes in the microbial culture.

It is recognised the optimum supply of a substrate may also be dependant on the fermentation operational requirements. For example, in batch fermentation (or a batch phase start-up of a continuous culture) it may be desirable to provide substrate such that there is no net production or consumption of acetate and there is no change in pH. In continuous operation, it may be desirable to continuously produce small amounts of acetate, such that a stable culture can be maintained.

Additionally or alternatively, accumulation and/or consumption of metabolites, such as acetate and other acids such as lactate or bases such as $NH_3$, can be monitored by any means known in the art and substrate supply controlled in response to metabolite levels. For example, acetate and/or lactate concentration in a fermenter can be periodically or substantially continuously monitored by a variety of analytical techniques, such as GC, HPLC, GCIR, GCMS, LCMS, NIR via one or more selective probe(s), such as amperomic probes or other suitable assays, familiar to those skilled in the art. Metabolite concentrations can be monitored in the fermentation media in the bioreactor and/or in media exiting the bioreactor (such as the product stream from a continuous fermentation) and substrate levels optimised based on the metabolites measured in the media. For example, if acetate starts to accumulate in the media above a predetermined threshold, substrate supply can increase in accordance with the methods of the invention. Similarly, if acetate concentration decreases below a predetermined or preset threshold, substrate supply can be decreased. In particular embodiments, at steady state, when the substrate is provided at or toward an optimum level, acetate is maintained within a predetermined concentration range of approximately 1-10 g/L, or approximately 2-8 g/L, or approximately 3-7 g/L, or approximately 4-6 g/L.

In particular embodiments, at steady state, when the substrate is provided at or toward an optimum level, acetate is maintained at a concentration of approximately 10 g/L, or approximately 9 g/L, or approximately 8 g/L, or approximately 7 g/L, or approximately 6 g/l, or approximately 5 g/L in the fermentation broth. in particular embodiments, a substrate is provided at or toward an optimum level, when the culture produces acid(s), such as acetate, at a specific rate of less than 2 g/g biomass/day, or less than 1.5 g/g/day, or less than 1.2 g/g/day, or less than 1 g/g/day.

Thus, in accordance with the methods of the invention, media pH can be used as an indication that the culture is supplied with a substantially optimal amount of substrate, or at least within an optimal range. Furthermore, by maintaining the media at a desired pH or within a predetermined pH range, substrate supply, particularly supply of a substrate comprising CO, can be optimised.

According to particular aspects of the invention, the method of improving microbial fermentation includes monitoring hydrogen ($H_2$) production by a microbial culture and controlling supply of a substrate based on $H_2$ production. In particular embodiments $H_2$ is produced by one or more carboxydotrophic microorganisms when a substrate comprising CO and minimal or no $H_2$ is provided at or toward an optimum level or range. In particular embodiments of the invention, during periods of limited substrate supply, carboxydotrophic bacteria, such as *Clostridium autoethanogenum*, convert a portion of the substrate into products such as acid(s) and small amounts of alcohol(s) and a further portion is directed to anabolic production of cellular material (growth). During such times of limited substrate supply, $H_2$ is substantially not produced. It has been surprisingly recognised that when the substrate supply is increased towards an optimal level, carboxydotrophic bacteria, such as *C. autoethanogenum*, convert a portion of the substrate into products such as acid(s) and alcohol(s), a portion into cellular material and a further portion into $H_2$. In particular embodiments, when a substrate, particularly a substrate comprising CO, is provided at or towards an an optimum level, or within an optimum range, $H_2$ is produced in addition to desired metabolites such as ethanol. It is also recognised that oversupply of a substrate comprising CO can lead to inhibition of hydrogenase enzyme(s), thus reducing the amount of $H_2$ produced by the culture. Thus, in accordance with the invention, the substrate can be provided at or about an optimal level, or within an optimal range by monitoring $H_2$ produced by the culture.

In particular embodiments, wherein the substrate comprises CO, as the substrate availability increases above an optimal amount (or above an optimum range), excess CO inhibits hydrogenase enzyme(s), thus substantially preventing $H_2$ production. As hydrogenase enzyme(s) are inhibited, the microbe cannot relieve itself of excess reducing power, thus leading to culture problems such as growth inhibition and/or microbial death.

Thus, in accordance with the methods of the invention, hydrogen produced by a microbial culture can be used as an indication that the culture is supplied with a substantially optimal amount of substrate, or at least within an optimal range. Furthermore, hydrogen production by a microbial culture can be used to control substrate supply to the microbial culture. For example, substrate supply to a substrate limited culture can be increased until hydrogen production is observed. Following initiation of hydrogen production, substrate supply can be adjusted to maintain hydrogen production over time. As a microbial culture grows, the substrate supply can be increased to maintain hydrogen production.

This control method is of particular importance in a growing microbial culture, as the substrate requirement of the culture will change over time. For example, an optimal level of substrate at one time point may be a limiting amount of substrate at a later time point, if the culture has grown. It is considered during exponential growth, the optimum amount of substrate required will also increase substantially exponentially.

It is recognised that the hydrogenase enzymes are reversible, so a microbial culture can use a hydrogen component of a substrate stream comprising hydrogen as an energy source. Thus, in particular embodiments, the methods of optimisation employ a substrate comprising CO that contains minimal amounts of hydrogen or is substantially hydrogen free.

DEFINITIONS

Unless otherwise defined, the following terms as used throughout this specification are defined as follows:

The terms "increasing the efficiency", "increased efficiency" and the like, when used in relation to a fermentation process, include, but are not limited to, increasing one or more of: the rate of growth of micro-organisms catalysing the fermentation, the volume of desired product (such as alcohols) produced per volume of substrate (such as carbon monoxide) consumed, the rate of production or level of production of the desired product, and the relative proportion of the desired product produced compared with other by-products of the fermentation. Similarly, "optimisation" or the like includes increasing the efficiency towards a maximum efficiency given a particular set of fermentation conditions.

The term "substrate comprising carbon monoxide" and like terms should be understood to include any substrate in which carbon monoxide is available to one or more strains of bacteria for growth and/or fermentation, for example.

"Gaseous substrate comprising carbon monoxide" include any gas which contains carbon monoxide. The gaseous substrate will typically contain a significant proportion of CO, preferably at least about 5% to about 100% CO by volume.

In the context of fermentation products, the term "acid" as used herein includes both carboxylic acids and the associated carboxylate anion, such as the mixture of free acetic acid and acetate present in a fermentation broth as described herein. The ratio of molecular acid to carboxylate in the fermentation broth is dependent upon the pH of the system. The term "acetate" includes both acetate salt alone and a mixture of molecular or free acetic acid and acetate salt, such as the mixture of acetate salt and free acetic acid present in a fermentation broth as may be described herein. The ratio of molecular acetic acid to acetate in the fermentation broth is dependent upon the pH of the system.

The term "bioreactor" includes a fermentation device consisting of one or more vessels and/or towers or piping arrangements, which includes the Continuous Stirred Tank Reactor (CSTR), Immobilized Cell Reactor (ICR), Trickle Bed Reactor (TBR), Moving Bed Biofilm Reactor (MBBR), Bubble Column, Gas Lift Fermenter, Membrane Reactor such as Hollow Fibre Membrane Bioreactor (HFMBR), Static Mixer, or other vessel or other device suitable for gas-liquid contact.

The term "mass transfer" as used herein relates to the transfer of atoms or molecules, particularly substrate atoms or molecules from a gaseous phase into an aqueous solution.

Unless the context requires otherwise, the phrases "fermenting", "fermentation process" or "fermentation reaction" and the like, as used herein, are intended to encompass both the growth phase and product biosynthesis phase of the process. As will be described further herein, in some embodiments the bioreactor may comprise a first growth reactor and a second fermentation reactor. As such, the addition of metals or compositions to a fermentation reaction should be understood to include addition to either or both of these reactors.

While the following description focuses on particular embodiments of the invention, namely the production of ethanol and/or acetate using CO as the primary substrate, it should be appreciated that the invention may be applicable to production of alternative alcohols and/or acids and the use of alternative substrates as will be known by persons of ordinary skill in the art to which the invention relates. For example, gaseous substrates containing carbon dioxide and hydrogen may be used. Further, the invention may be applicable to fermentation to produce butyrate, propionate, caproate, ethanol, propanol, and butanol. The methods may also be of use in producing hydrogen. By way of example, these products may be produced by fermentation using microbes from the genus *Moorella*, *Clostridia*, *Ruminococcus*, *Acetobacterium*, *Eubacterium*, *Butyribacterium*, *Oxobacter*, *Methanosarcina*, *Methanosarcina*, and *Desulfotomaculum*.

Certain embodiments of the invention are adapted to use gas streams produced by one or more industrial processes. Such processes include steel making processes, particularly processes which produce a gas stream having a high CO content or a CO content above a predetermined level (i.e., 5%). According to such embodiments, acetogenic bacteria are preferably used to produce acids and/or alcohols, particularly ethanol or butanol, within one or more bioreactors. Those skilled in the art will be aware upon consideration of the instant disclosure that the invention may be applied to various industries or waste gas streams, including those of vehicles with an internal combustion engine. Also, those skilled in the art will be aware upon consideration of the instant disclosure that the invention may be applied to other fermentation reactions including those using the same or different micro-organisms. It is therefore intended that the scope of the invention is not limited to the particular embodiments and/or applications described but is instead to be understood in a broader sense; for example, the source of the gas stream is not limiting, other than that at least a component thereof is usable to feed a fermentation reaction. The invention has particular applicability to improving the overall carbon capture and/or production of ethanol and other alcohols from gaseous substrates such as automobile exhaust gases and high volume CO-containing industrial flue gases.

Fermentation

Processes for the production of ethanol and other alcohols from gaseous substrates are known. Exemplary processes include those described for example in WO2007/117157, WO2008/115080, U.S. Pat. No. 6,340,581, U.S. Pat. No. 6,136,577, U.S. Pat. No. 5,593,886, U.S. Pat. No. 5,807,722 and U.S. Pat. No. 5,821,111, each of which is incorporated herein by reference.

A number of carboxydotrophic anaerobic bacteria are known to be capable of carrying out the fermentation of CO to alcohols, including n-butanol and ethanol, and acetic acid, and are suitable for use in the process of the present invention. Examples of such bacteria that are suitable for use in the invention include those of the genus *Clostridium*, such as strains of *Clostridium ljungdahlii*, including those described in WO 00/68407, EP 117309, U.S. Pat. Nos. 5,173,429, 5,593,886, and 6,368,819, WO 98/00558 and WO 02/08438, *Clostridium carboxydivorans* (Liou et al., International Journal of Systematic and Evolutionary Microbiology 33: pp 2085-2091), *Clostridium ragsdalei* (WO/2008/028055) and *Clostridium autoethanogenum* (Abrini et al, Archives of Microbiology 161: pp 345-351). Other suitable bacteria include those of the genus *Moorella*, including *Moorella* sp HUC22-1, (Sakai et al, Biotechnology Letters 29: pp 1607-1612), and those of the genus *Carboxydothermus* (Svetlichny, V. A., Sokolova, T. G. et al (1991), Systematic and Applied Microbiology 14: 254-260). Further examples include *Moorella thermoacetica*, *Moorella thermoautotrophica*, *Ruminococcus productus*, *Acetobacterium woodii*, *Eubacterium limosum*, *Butyribacterium methylotrophicum*, *Oxobacter pfennigii*, *Methanosarcina barkeri*, *Methanosarcina acetivorans*, *Desulfotomaculum kuznetsovii* (Simpa et. al. Critical Reviews in Biotechnology, 2006 Vol. 26. Pp41-65). In addition, it should be understood that other carboxydotrophic and/or acetogenic anaerobic bacteria may be applicable to the present invention as would be understood by a person of skill in the art. It will also be appreciated that the invention may be applied to a mixed culture of two or more bacteria.

One exemplary micro-organism suitable for use in the present invention is *Clostridium autoethanogenum*. In one embodiment, the *Clostridium autoethanogenum* is a *Clostridium autoethanogenum* having the identifying characteristics of the strain deposited at the German Resource Centre for Biological Material (DSMZ) under the identifying deposit number 19630. In another embodiment, the *Clostridium autoethanogenum* is a *Clostridium autoethano-*

*genum* having the identifying characteristics of DSMZ deposit number DSMZ 10061.

Culturing of the bacteria used in the methods of the invention may be conducted using any number of processes known in the art for culturing and fermenting substrates using anaerobic bacteria. Exemplary techniques are provided in the "Examples" section below. By way of further example, those processes generally described in the following articles using gaseous substrates for fermentation may be utilised: (i) K. T. Klasson, et al. (1991). Bioreactors for synthesis gas fermentations resources. Conservation and Recycling, 5; 145-165; (ii) K. T. Klasson, et al. (1991). Bioreactor design for synthesis gas fermentations. Fuel. 70. 605-614; (iii) K. T. Klasson, et al. (1992). Bioconversion of synthesis gas into liquid or gaseous fuels. Enzyme and Microbial Technology. 14; 602-608; (iv) J. L. Vega, et al. (1989). Study of Gaseous Substrate Fermentation: Carbon Monoxide Conversion to Acetate. 2. Continuous Culture. Biotech. Bioeng. 34. 6. 785-793; (v) J. L. Vega, et al. (1989). Study of gaseous substrate fermentations: Carbon monoxide conversion to acetate. 1. Batch culture. Biotechnology and Bioengineering. 34. 6. 774-784; (vi) J. L. Vega, et al. (1990). Design of Bioreactors for Coal Synthesis Gas Fermentations. Resources, Conservation and Recycling. 3. 149-160; all of which are incorporated herein by reference.

The fermentation may be carried out in any suitable bioreactor, such as a continuous stirred tank reactor (CSTR), an immobilised cell reactor, a gas-lift reactor, a bubble column reactor (BCR), a membrane reactor, such as a Hollow Fibre Membrane Bioreactor (HFMBR) or a trickle bed reactor (TBR). Also, in some embodiments of the invention, the bioreactor may comprise a first, growth reactor in which the micro-organisms are cultured, and a second, fermentation reactor, to which fermentation broth from the growth reactor is fed and in which most of the fermentation product (e.g. ethanol and acetate) is produced.

According to various embodiments of the invention, the carbon source for the fermentation reaction is a gaseous substrate containing CO. The substrate may be a CO-containing waste gas obtained as a by-product of an industrial process, or from some other source such as from automobile exhaust fumes. In certain embodiments, the industrial process is selected from the group consisting of ferrous metal products manufacturing, such as a steel mill, non-ferrous products manufacturing, petroleum refining processes, gasification of coal, electric power production, carbon black production, ammonia production, methanol production and coke manufacturing. In these embodiments, the CO-containing substrate may be captured from the industrial process before it is emitted into the atmosphere, using any convenient method. Depending on the composition of the CO-containing substrate, it may also be desirable to treat it to remove any undesired impurities, such as dust particles before introducing it to the fermentation. For example, the gaseous substrate may be filtered or scrubbed using known methods.

Alternatively, the CO-containing substrate may be sourced from the gasification of biomass. The process of gasification involves partial combustion of biomass in a restricted supply of air or oxygen. The resultant gas typically comprises mainly CO and $H_2$, with minimal volumes of $CO_2$, methane, ethylene and ethane. For example, biomass by-products obtained during the extraction and processing of foodstuffs such as sugar from sugarcane, or starch from maize or grains, or non-food biomass waste generated by the forestry industry may be gasified to produce a CO-containing gas suitable for use in the present invention.

The CO-containing substrate will typically contain a major proportion of CO, such as at least about 20% to about 100% CO by volume, from 40% to 95% CO by volume, from 40% to 70% CO by volume, and from 40% to 65% CO by volume. In particular embodiments, the substrate comprises 25%, or 30%, or 35%, or 40%, or 45%, or 50% CO by volume. Substrates having lower concentrations of CO, such as 6%, may also be appropriate, particularly when $H_2$ and $CO_2$ are also present.

While it is not necessary for the substrate to contain any hydrogen, the presence of $H_2$ should not be detrimental to product formation in accordance with methods of the invention. In particular embodiments, the substrate stream comprises low concentrations of H2, for example, less than 5%, or less than 4%, or less than 3%, or less than 2%, or less than 1%, or is substantially hydrogen free. The substrate may also contain some $CO_2$ for example, such as about 1% to about 80% $CO_2$ by volume, or 1% to about 30% $CO_2$ by volume.

In particular embodiments, wherein pH is used to control substrate supply, the substrate may comprise substantial amounts of H2. In particular embodiments, the presence of hydrogen results in an improved overall efficiency of alcohol production. For example, in particular embodiments, the substrate may comprise an approx 2:1, or 1:1, or 1:2 ratio of H2:CO.

Typically, the carbon monoxide will be added to the fermentation reaction in a gaseous state. However, the methods of the invention are not limited to addition of the substrate in this state. For example, the carbon monoxide can be provided in a liquid. For example, a liquid may be saturated with a carbon monoxide containing gas and that liquid added to the bioreactor. This may be achieved using standard methodology. By way of example a microbubble dispersion generator (Hensirisak et. al. Scale-up of microbubble dispersion generator for aerobic fermentation; *Applied Biochemist and Biotechnology Volume* 101, Number 3/October, 2002) could be used for this purpose.

Typically a gaseous substrate will be supplied to an aqueous fermentation broth comprising one or more microorganisms such that effective mass transfer across the gas/liquid interface occurs. Many methods are known to increase efficiency of mass transfer of a substrate comprising CO into an aqueous fermentation broth, all of which are incorporated herein as if individually specified. In particular embodiments the rate of mass transfer of the substrate comprising CO is controlled such that the substrate is provided at or toward an optimum rate in accordance of the methods of the invention.

It will be appreciated that for growth of the bacteria and CO-to-alcohol fermentation to occur, in addition to the CO-containing substrate gas, a suitable liquid nutrient medium will need to be fed to the bioreactor. A nutrient medium will contain vitamins and minerals sufficient to permit growth of the micro-organism used. Anaerobic media suitable for the fermentation of ethanol using CO as the sole carbon source are known in the art. For example, suitable media are described in U.S. Pat. Nos. 5,173,429 and 5,593,886 and WO 02/08438, WO2007/115157, WO2008/115080 and WO2009/022925 referred to above.

The fermentation should desirably be carried out under appropriate conditions for the desired fermentation to occur (e.g. CO-to-ethanol). Reaction conditions that should be considered include pressure, temperature, gas flow rate, liquid flow rate, media pH, media redox potential, agitation rate (if using a continuous stirred tank reactor), inoculum level, maximum gas substrate concentrations to ensure that CO in the liquid phase does not become limiting, and maximum product concentrations to avoid product inhibition. Suitable conditions are described in WO02/08438, WO07/117,157, WO2008/115080 and WO2009/022925.

The optimum reaction conditions will depend partly on the particular micro-organism used. However, in particular embodiments, the fermentation is conducted at pressure higher than ambient pressure. Operating at increased pressures allows a significant increase in the rate of CO transfer from the gas phase to the liquid phase where it can be taken up by the micro-organism as a carbon source for the production of ethanol. This in turn means that the retention time (defined as the liquid volume in the bioreactor divided by the input gas flow rate) can be reduced when bioreactors are maintained at elevated pressure rather than atmospheric pressure.

It is recognised that mass transfer rate of CO into an aqueous media is proportional to the partial pressure of a gaseous substrate comprising CO. As such, the mass transfer rate can be increased by increasing the proportion of CO in a gas stream by enrichment or removal of unwanted components, such as inert components. Additionally, partial pressure of CO can be increasing the pressure of a gaseous substrate stream.

The benefits of conducting a gas-to-ethanol fermentation at elevated pressures have also been described elsewhere. For example, WO 02/08438 describes gas-to-ethanol fermentations performed under pressures of 30 psig and 75 psig, giving ethanol productivities of 150 g/l/day and 369 g/l/day respectively. However, example fermentations performed using similar media and input gas compositions at atmospheric pressure were found to produce between 10 and 20 times less ethanol per liter per day.

It is also desirable that the rate of introduction of the CO-containing gaseous substrate is such as to ensure that the concentration of CO in the liquid phase does not become limiting. This is because a consequence of CO-limited conditions may be that the ethanol product is consumed by the culture.

Product Recovery

The products of the fermentation reaction can be recovered using known methods. Exemplary methods include those described in WO07/117,157, WO08/115,080, U.S. Pat. No. 6,340,581, U.S. Pat. No. 6,136,577, U.S. Pat. No. 5,593,886, U.S. Pat. No. 5,807,722 and U.S. Pat. No. 5,821,111. However, briefly and by way of example only ethanol may be recovered from the fermentation broth by methods such as fractional distillation or evaporation, and extractive fermentation.

Distillation of ethanol from a fermentation broth yields an azeotropic mixture of ethanol and water (i.e., 95% ethanol and 5% water). Anhydrous ethanol can subsequently be obtained through the use of molecular sieve ethanol dehydration technology, which is also well known in the art.

Extractive fermentation procedures involve the use of a water-miscible solvent that presents a low toxicity risk to the fermentation organism, to recover the ethanol from the dilute fermentation broth. For example, oleyl alcohol is a solvent that may be used in this type of extraction process. Oleyl alcohol is continuously introduced into a fermenter, whereupon this solvent rises forming a layer at the top of the fermenter which is continuously extracted and fed through a centrifuge. Water and cells are then readily separated from the oleyl alcohol and returned to the fermenter while the ethanol-laden solvent is fed into a flash vaporization unit. Most of the ethanol is vaporized and condensed while the oleyl alcohol is non volatile and is recovered for re-use in the fermentation.

Acetate, which is produced as a by-product in the fermentation reaction, may also be recovered from the fermentation broth using methods known in the art.

For example, an adsorption system involving an activated charcoal filter may be used. In this case, it is preferred that microbial cells are first removed from the fermentation broth using a suitable separation unit. Numerous filtration-based methods of generating a cell free fermentation broth for product recovery are known in the art. The cell free ethanol—and acetate—containing permeate is then passed through a column containing activated charcoal to adsorb the acetate. Acetate in the acid form (acetic acid) rather than the salt (acetate) form is more readily adsorbed by activated charcoal. It is therefore preferred that the pH of the fermentation broth is reduced to less than about 3 before it is passed through the activated charcoal column, to convert the majority of the acetate to the acetic acid form.

Acetic acid adsorbed to the activated charcoal may be recovered by elution using methods known in the art. For example, ethanol may be used to elute the bound acetate. In certain embodiments, ethanol produced by the fermentation process itself may be used to elute the acetate. Because the boiling point of ethanol is 78.8° C. and that of acetic acid is 107° C., ethanol and acetate can readily be separated from each other using a volatility-based method such as distillation.

Other methods for recovering acetate from a fermentation broth are also known in the art and may be used in the processes of the present invention. For example, U.S. Pat. Nos. 6,368,819 and 6,753,170 describe a solvent and cosolvent system that can be used for extraction of acetic acid from fermentation broths. As with the example of the oleyl alcohol-based system described for the extractive fermentation of ethanol, the systems described in U.S. Pat. Nos. 6,368,819 and 6,753,170 describe a water immiscible solvent/co-solvent that can be mixed with the fermentation broth in either the presence or absence of the fermented micro-organisms in order to extract the acetic acid product. The solvent/co-solvent containing the acetic acid product is then separated from the broth by distillation. A second distillation step may then be used to purify the acetic acid from the solvent/co-solvent system.

The products of the fermentation reaction (for example ethanol and acetate) may be recovered from the fermentation broth by continuously removing a portion of the broth from the fermentation bioreactor, separating microbial cells from the broth (conveniently by filtration), and recovering one or more product from the broth simultaneously or sequentially. In the case of ethanol it may be conveniently recovered by distillation, and acetate may be recovered by adsorption on activated charcoal, using the methods described above. The separated microbial cells can be returned to the fermentation bioreactor. The cell free permeate remaining after the ethanol and acetate have been removed is also preferably returned to the fermentation bioreactor. Additional nutrients (such as B vitamins) may be added to the cell free permeate to replenish the nutrient medium before it is returned to the bioreactor. Also, if the pH of the broth was adjusted as described above to enhance adsorption of acetic acid to the activated charcoal, the pH should be re-adjusted to a similar pH to that of the broth in the fermentation bioreactor, before being returned to the bioreactor.

Controlling Substrate Supply

According to some aspects of the invention, there are provided methods of improving overall efficiency of microbial fermentation of a substrate, the method comprising providing the substrate substantially at an optimum level, towards an optimum level or within an optimum range. In particular embodiments of the invention, the substrate comprises CO and is provided to one or more carboxydotrophic bacteria, such as acetogenic bacteria. Under suitable anaerobic conditions, acetogenic bacteria, such as *Clostridium autoethano-* genum, *Clostridium ljungdahlii*, *Clostridium ragsdalei* and *Clostridium carboxydivorans* convert a substrate comprising CO into products including acids and alcohols. In accordance with particular embodiments, the invention provides methods of optimising microbial fermentation of a substrate, particularly a substrate comprising CO, by controlling the supply of the substrate, such that it is provided at an optimum level, towards an optimum level or within an optimum range, to promote culture viability and production of desirable metabolites such as ethanol.

It has been recognised that increasing the amount of substrate available to the microbial culture, for conversion to products, toward an optimum level or range leads to increases in microbial growth rate, metabolite production rate and/or the amount of alcohol(s) produced, relative to acid(s). In particular embodiments of the invention, products are produced such that a desirable product ratio of at least 1:1; or at least 1:2; or at least 1:3; or at least 1:4; or at least 1:5; or at least 1:10; or at least 1:20; acid: alcohol is produced by the culture. In particular embodiments of the invention, alcohol (particularly ethanol) is produced without concomitant production of acid (particularly acetate).

In particular embodiments, the microbial culture is not able to regulate substrate uptake. Thus, an oversupply of substrate leads to culture problems, such as growth inhibition and/or microbial death.

A substrate comprising CO is typically provided in gaseous form and availability of CO to a microbial culture will be dependent upon the mass transfer properties of the fermentation system. For example, availability of CO to a microbial culture suspended in a fermentation broth is dependent on factors known to those skilled in the art including temperature, broth composition, gas supply rate, gas composition, CO vapour pressure, mixing. Thus, increasing availability of CO to a microbial fermentation requires improving mass transfer properties of the system, such as increasing substrate supply rate and/or increasing agitation of a mechanically stirred bioreactor.

In order to maintain culture viability, microbial growth and/or production of desirable products, such as alcohols, the substrate should be made available to the culture at an optimum level, towards an optimum level or within an optimum range. A microbial culture with an inadequate (sub-optimal) supply of CO may grow poorly, be less viable and/or produce predominantly less desirable products, such as acid(s), in particular acetate. Furthermore, the growth rate and metabolite production rate can also be substantially lower than a microbial culture supplied with an adequate or optimised amount of substrate. In particular embodiments, the microbial culture is not able to regulate substrate uptake. Thus, an oversupply of substrate leads to culture problems, such as growth inhibition and/or microbial death.

It has been recognised that increasing the amount of substrate available to the microbial culture, for conversion to products, toward an optimum level leads to an increase in the amount of alcohol(s) produced, relative to acid(s). In particular embodiments of the invention, alcohol (particularly ethanol) is produced without concomitant production of acid (particularly acetate).

The invention provides a method of controlling supply of a substrate, particularly a substrate comprising CO, such that the substrate is substantially continuously provided at an optimum level, towards an optimum level or within an optimum range. According to particular embodiments, substrate is provided at an optimum level, or within an optimum range, by maintaining pH of the fermentation media at a constant level or within a constant range or within a predetermined rate of change.

It has been recognised that increasing the amount of substrate available to the microbial culture, for conversion to products, toward an optimum level leads to an increase in the amount of alcohol(s) produced, relative to acid(s).

In other embodiments, a microbial culture may produce or consume one or more acidic and/or basic components such that pH changes during optimum operation. Thus, in accordance with the invention, substrate can be supplied such that pH changes substantially at or toward a predetermined rate of change. In such embodiments, sustainable microbial growth and desired metabolite production will be associated with production and/or consumption of one or more acids and/or bases, such that there is a net change in pH over time. In particular embodiments, carboxydotrophic microorganisms, such as *Clostridium autoethanogenum*, produce alcohol (such as ethanol) and acids (such as acetate) concurrently. In particular embodiments of the invention, products are produced such that a desirable product ratio of at least 1:1; or at least 1:2; or at least 1:3; or at least 1:4; or at least 1:5; or at least 1:10; or at least 1:20; acid: alcohol is produced by the culture. Furthermore, there may also be a pH change associated with consumption of basic components such as NH3. Thus, in particular embodiments, during steady state continuous fermentation, there will be a net decrease in pH unless the pH is controlled through the addition of a base or continuous addition of fresh media with a pH suitable to maintain a constant pH.

The pH of a fermentation system is typically affected by the production of acid compounds such as acetate and/or lactate and to a lesser extent by the consumption of basic or acid compounds such as NH3, phosphate etc. The rate of pH change will be dependent on the rate at which the such production and/or consumption of acidic/basic compounds takes place. In particular embodiments, acetogenic microbes produce acetate as a metabolite and this accounts for the largest change in pH over time.

For a given fermentation system, a rate of pH change can be determined experimentally when a substrate is supplied at an optimum rate. For example, when a culture of one or more carboxydotrophic microorganisms is provided substrate at or toward an optimum level, ethanol and acetate may be produced at particular rates. The pH of the fermentation broth will change in accordance with the amount of acetate present and to a lesser extent, the amount of other acid or basic components such as NH3 present. It is recognised the rate of change of pH will be dependent on the buffering capacity of the fermentation broth and the pH start point. For example, acetate accumulation in a well buffered fermentation broth will lead to small and/or slow changes in pH. Conversely, acetate accumulation in a substantially in buffered fermentation broth will lead to large and/or rapid changes in pH. Thus, rate of change of pH at optimum substrate supply should be predetermined for any given fermentation system.

It is also recognised that small changes in pH can have a detrimental effect on fermentation. Accordingly, pH change through acid production can be counteracted by the addition of base, such as NH4OH. As such, pH of a continuously operated fermentation system can be maintained within optimum pH operating parameters. For example, the optimum operating pH of *Clostridium autoethanogenum* has been experimentally determined to be approximately 5-5.5. In particular embodiments, the desirable range is ±0.5 units of the optimum operating pH. Optimum operating pH for various carboxydotrophic bacteria is described in Henstra et al. *Current Opinion in Biotechnology*, 2007, 18:200-206.

As such, control over substrate provision can be maintained using several alternative mechanisms. For example, by determining the rate of change of pH, by determining the amount of acid/base required to counteract the pH change or by determining the amount of acetate produced by the culture.

Thus, under steady state conditions, acid is produced at a substantially constant rate, resulting in a substantially constant concentration in the fermentation broth. In particular embodiments, there is provided a method of optimising supply of a substrate comprising CO to a bioreactor, wherein the substrate is fermented to produce products including one or more alcohol(s) and/or acid(s) by a culture of one or more carboxydotrophic microorganisms, the method including determining acid levels in the bioreactor at a first time point and a second time point, wherein a change in acid level between the first and second time points results in a change in substrate supply. Thus, if the level acid (acetate) increases over time, substrate supply can be increased such that acid production slows, bringing the acid back to a desired level or range over time. Conversely, if the level of acid decreases, substrate supply can be decreased, thus promoting acid production. In particular embodiments, acetate is maintained at a substantially constant concentration of approximately 10 g/L, or approximately 9 g/L, or approximately 8 g/L, or approximately 7 g/L, approximately 6 g/L, or approximately 5 g/L fermentation broth. In particular embodiments, the acetate is maintained within a predetermined concentration range, such as approximately 1-10 g/L, or approximately 2-8 g/L, or approximately 3-7 g/L, or approximately 4-6 g/L fermentation broth.

It is also recognised, in particular embodiments, that the rate of production of one or more acid(s) such as acetate is dependent on the microbial density in a fermentation broth. In particular embodiments, the specific productivity of acetate is maintained at less than 2 g/g biomass/day, or less than 1.5 g/g/day, or less than 1.2 g/g/day, or less than 1 g/g/day.

In another particular embodiment of the invention, alcohol (particularly ethanol) is produced without concomitant production of acid (particularly acetate). Accordingly, when substrate, particularly a substrate comprising CO, is provided at an optimum level or within an optimum range, there is no net change in acid concentration(s) in the media and the pH of the media remains substantially constant. In such embodiments, the rate of change of pH will be approximately 0.

It is recognised that the product ratio may also be related in part to media composition as described in Gaddy U.S. Pat. No. 7,285,402 which is fully incorporated here by reference. As such it is recognised that the desired product ratio may change from one fermentation system to another. Accordingly the rate of change of pH associated with supply of the optimum substrate level will also change.

If the culture becomes substrate limited at any stage of the fermentation, the culture produces acid(s), such as acetate, causing the pH of fermentation broth to decrease. Thus, in accordance with the methods of the invention, the substrate supply can be increased such that net acetate accumulation ceases and pH stabilises.

Additionally or alternatively, if substrate is oversupplied, there is a net consumption of acid(s), as acetate is converted to ethanol and the pH increases. Thus, the substrate supply should be decreased such that net acid consumption ceases and the pH stabilises. It is noted that substrate oversupply for an extended period can lead to culture problems such as growth inhibition and/or microbial death.

In particular embodiments, the substrate is provided such that pH is maintained within a desirable range. Those skilled in the art will appreciate a suitable pH or pH range for conducting a particular fermentation. In particular embodiments, for example embodiments wherein *Clostridium autoethanogenum* is used to produce products, the substrate is provided such that pH is maintained between 5-6; or between 5.1-5.9; or within 5.2-5.8; or between 5.3-5.7; or between 5.4-5.6; or substantially at 5.5.

pH can be determined by any known means. However, by way of example, electrode probes are typically used to measure pH during fermentation and examples of such probes will be known to those skilled in the art.

By way of non-limiting example, consider a microbial culture under the following conditions:

Limited Substrate:

a. The culture has enough substrate to grow and produce products (predominantly acid(s)) but will not produce significant amounts of desirable products (such as alcohol(s)). pH decreases faster than a predetermined rate of change. Therefore increase substrate supply toward optimal level Optimal Substrate Supply b. The culture has enough substrate to grow and produce products, particularly desirable products such as alcohol(s) at high rates (at or at least towards the optimum productivity rates). pH changes at a predetermined rate of change. Therefore maintain substrate supply at optimal level Oversupply of Substrate c. Acid(s), such as acetate converted into alcohols, such as ethanol. Growth inhibition and microbial death may occur. pH decreases slower than a predetermined rate of change, or increases. Therefore decrease to optimal level Thus, the microbial culture in scenario 1 (above) should be provided with increasing amounts of substrate until pH stabilises, or returned to a predetermined level. Such a culture is considered to be provided with an optimum amount of substrate as in scenario 2. Under batch conditions, it is considered such a culture will grow until it becomes limited again, thus the growing culture should be provided increasing amounts of substrate over time, such that pH is substantially maintained constant or within a predetermined range. If, at any time, substrate is oversupplied (scenario 3), pH increases and the substrate supply must be decreased back towards the optimum for efficient growth and metabolite production to resume.

It is recognised that other acidic metabolites, such as lactate may be produced by a microbial culture, particularly during periods of substrate oversupply. Thus, in particular embodiments, the method includes monitoring metabolite concentrations in a fermentation media, in addition to monitoring pH. Those skilled in the art will appreciate methods of monitoring metabolite concentrations in a fermentation media. However, by way of example, analytical methods, such as GC, GCIR, GCMS, LCMS, HPLC, NIR can be used.

According to some aspects of the invention, there are provided methods of improving overall efficiency of microbial fermentation of a substrate, the method comprising providing the substrate substantially at an optimum level, towards an optimum level or within an optimum range. In particular embodiments of the invention, the substrate comprises CO and is provided to one or more carboxydotrophic bacteria, such as acetogenic bacteria. Under suitable anaerobic conditions, acetogenic bacteria, such as *Clostridium autoethanogenum*, *Clostridium ljungdahlii*, *Clostridium ragsdalei* and *Clostridium carboxydivorans* convert a substrate comprising CO into products including acids and alcohols. In accordance with particular embodiments, the invention provides methods of optimising microbial fermentation of a substrate, particularly a substrate comprising CO, by controlling the supply of the substrate, such that it is provided at an optimum level, towards an optimum level or within an optimum ranges, to promote culture viability and production of desirable metabolites such as ethanol. In particular embodiments the CO content of the gas comprising little or no H2, such as less than 5%, or less than 4%, or less than 3%, or less than 2%, or less than 1% or 0% H2.

A substrate comprising CO is typically provided in gaseous form and availability of CO to a microbial culture will be dependent upon the mass transfer properties of the fermentation system. For example, availability of CO to a microbial culture suspended in a fermentation broth is dependent on factors known to those skilled in the art including temperature, broth composition, gas supply rate, gas composition, CO vapour pressure, mixing. Thus, increasing availability of CO to a microbial fermentation requires improving mass transfer properties of the system, such as increasing substrate supply rate and/or increasing agitation of a mechanically stirred bioreactor.

In order to maintain culture viability, microbial growth and/or production of desirable products, such as alcohols, the substrate should be made available to the culture at an optimum level, towards an optimum level or within an optimum range. A microbial culture with an inadequate (sub-optimal) supply of CO may grow poorly, be less viable and/or produce predominantly less desirable products, such as acid(s), in particular acetate. Furthermore, the growth rate and metabolite production rate can also be substantially lower than a microbial culture supplied with an adequate or optimised amount of substrate.

The invention provides a method of controlling supply of a substrate, particularly a substrate comprising CO, such that the substrate is substantially continuously provided at an optimum level, towards an optimum level or within an optimum range. According to particular aspects of the invention, the method of improving microbial fermentation includes monitoring hydrogen production by a microbial culture and controlling supply of the substrate based on hydrogen production.

In particular embodiments, a microbial culture supplied with an optimal amount of substrate (or substrate within an optimal range) will grow and produce desirable products, such as alcohols, at an optimal rate. In addition to desirable metabolite production ratios, the microbial culture will also produce hydrogen. Typically small amounts of hydrogen will be produced, such as about 0.5-5 mol % of the substrate consumed by a microbial culture. In particular embodiments, a microbial culture is provided with an optimal amount of substrate when the amount of hydrogen produced is maintained at approximately 1-3% of the substrate consumed by the culture.

By way of non-limiting example, consider a microbial culture under the following conditions:

Limited Substrate:
d. The culture has enough substrate to grow and produce products (predominantly acid(s)) but will not produce significant amounts of desirable products (such as alcohol(s)). Insignificant amounts or NO HYDROGEN PRODUCED.

Optimal Substrate Supply
e. The culture has enough substrate to grow and produce products, particularly desirable products such as alcohol(s) at high rates (at or at least towards the optimum productivity rates). HYDROGEN PRODUCED.

Oversupply of Substrate
f. Growth inhibition and microbial death may occur. NO HYDROGEN PRODUCED.

In accordance with the invention, hydrogen produced by a microbial culture can be used as an indication that the culture is supplied with a substantially optimal amount of substrate, or at least within an optimal range. Furthermore, hydrogen production by a microbial culture can be used to control substrate supply to the microbial culture. For example, substrate supply to a substrate limited culture can be increased until hydrogen production is observed. Following initiation of hydrogen production, substrate supply can be adjusted to maintain hydrogen production over time.

Thus, the microbial culture in scenario 1 (above) should be provided with increasing amounts of substrate until hydrogen is produced by the culture. Such a culture is considered to be provided with an optimum amount of substrate as in scenario 2. Under batch conditions, it is considered such a culture will grow until it becomes limited again, thus the growing culture should be provided increasing amounts of substrate over time, such that H2 production is maintained. If, at any time, substrate is oversupplied (scenario 3), H2 production stops and the substrate supply must be decreased back towards the optimum for efficient growth and metabolite production to resume.

It is recognised that in particular embodiments, small amounts of hydrogen may be produced during scenario 1 and 3. However, in accordance with the methods of the invention, the amount of hydrogen produced by the culture increases as the substrate made available to the culture increases or decreases towards an optimum level (or towards an optimum range).

In particular embodiments, wherein the microbial culture comprises *Clostridium autoethanogenum*, the specific CO uptake during substrate limitation is typically 0.3-0.6 mmol CO consumed per gram of biomass per minute (mmol/g/min). Under these substrate limited conditions, a microbial culture comprising *C. autoethanogenum* produces no or minimal amounts of H2 (less than 0.5 mol % of the substrate consumed). As substrate availability increases the H2 produced by the culture increases to at least 0.5 mol %; or at least 1.0 mol %; or at least 1.5 mol %; or at least 2.0 mol % of the CO consumed by the culture. Typically, the specific uptake of the culture increases above about 0.6 mmol/g/min. Under the conditions described herein, a microbial culture comprising *C. autoethanogenum* has an optimal substrate supply when the specific uptake can be maintained at least 0.6 mmol/g/min but less than 1.2 mmol/g/min. When the specific uptake increases above 1.2 mmol/g/min, the substrate is oversupplied and H2 production decreases and the substrate supply should be reduced. If the substrate supply is not reduced, growth inhibition and cell death occur.

FIG. 1 is a schematic representation of a system 100, according to one embodiment of the invention. Substrate stream 1 enters the bioreactor 2 via a suitable conduit 3. Substrate stream 1 comprises CO and in certain embodiments, the substrate stream is a waste gas stream from an industrial process, such as the decarburisation of steel. Substrate stream 1 may be a constant stream in the sense that it is constantly supplied, but the content of the stream may vary over time.

Bioreactor 2 is configured to perform the desired fermentation reaction to produce products. According to certain embodiments, bioreactor 2 is configured to convert CO into products including one or more acids and/or alcohols. Bioreactor 2 may comprise more than one tank, each tank configured to perform the same reaction and/or different stages within a particular fermentation process and/or different reactions, including different reactions for different fermentations that may include one or more common stages.

The products produced in bioreactor 2, such as acids and/or alcohols, may be recovered by any recovery process known in the art.

pH of the fermentation media can be monitored by pH measurement means 4. Thus, an operator can optionally make adjustments to microbial culture in bioreactor 2 and/or the substrate stream 1 using adjustment means 5 to maintain the microbial culture at, or transition the culture such that the substrate is supplied at an optimum level, towards an optimum level, or within an optimum range, in response to pH changes. Adjustments to the level of CO provided to the culture includes one or more of: changing CO concentration of the fermentation broth; changing composition of the substrate stream; changing pressure of the substrate stream; fermentation broth agitation rate. Additionally or alternatively, system 100 includes optional processing means 6 adapted to determine pH of the fermentation broth and control adjustment means 5, such that the substrate is supplied to the microbial culture at an optimum level, or within an optimum range. Furthermore, adjustments means 5 can be configured to make continuous adjustments or adjustments at discrete time points if necessary.

In another embodiment, 4 is a determining means configured to determine the concentration of acid, such as acetate, in the bioreactor 2. If the concentration of acid is determined to be above a predetermined threshold, the adjustment means 5 can increase the substrate supplied to the bioreactor 2. Any known determining means may be used to measure the concentration of acid in the bioreactor 2. However, by way of example, HPLC, GCMS, LCMS and/or NIR may be used.

Figure 2:
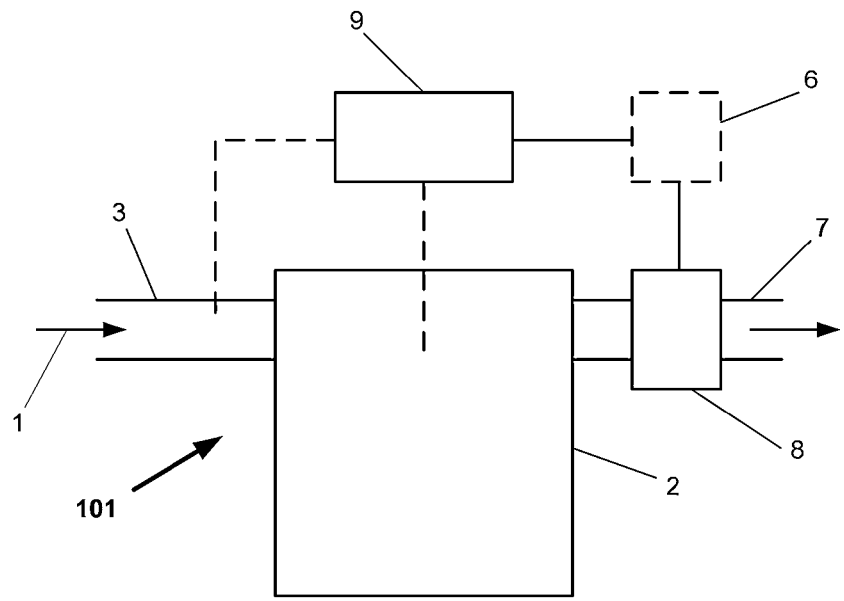
FIG. 2: is a schematic representation according to one embodiment of the invention.

FIG. 2 is a schematic representation of a system 101, according to one embodiment of the invention. Substrate stream 1 enters the bioreactor 2 via a suitable conduit 3. Substrate stream 1 comprises CO and in certain embodiments, the substrate stream is a waste gas stream from an industrial process, such as the decarburisation of steel. Substrate stream 1 may be a constant stream in the sense that it is constantly supplied, but the content of the stream may vary over time. In particular embodiments the substrate stream comprises little or no H2 such as less than 5%, or less than 4%, or less than 3%, or less than 2%, or less than 1% or 0% H2.

Bioreactor 2 is configured to perform the desired fermentation reaction to produce products. According to certain embodiments, bioreactor 2 is configured to convert CO into products including one or more acids and/or alcohols. Bioreactor 2 may comprise more than one tank, each tank configured to perform the same reaction and/or different stages within a particular fermentation process and/or different reactions, including different reactions for different fermentations that may include one or more common stages.

The products produced in bioreactor 2, such as acids and/or alcohols, may be recovered by any recovery process known in the art.

Components of the substrate stream that are unconsumed in the fermentation reaction and any by-products of the fermentation reaction, such as CO2 and H2, exit bioreactor 2 via exhaust outlet 7. In particular embodiments of the invention, measuring means 8 is adapted to determine the H2 and optionally CO and CO2 concentration in the exhausted stream exiting bioreactor 2 via exhaust outlet 4. In particular embodiments, the amount of hydrogen produced by the microbial culture is determined. Accordingly, an operator can optionally make adjustments to microbial culture in bioreactor 2 and/or the substrate stream 1 using adjustment means 9 to maintain the microbial culture at, or transition the culture such that the substrate is supplied at an optimum level, towards an optimum level, or within an optimum range. Adjustments to maintain or transition the culture includes one or more of: changing CO concentration of the fermentation broth; changing composition of the substrate stream; changing pressure of the substrate stream; fermentation broth agitation rate. Additionally or alternatively, system 101 includes optional processing means 6 adapted to determine hydrogen concentration of the exhaust stream and control adjustment means 9, such that the substrate is supplied to the microbial culture at an optimum level, or within an optimum range.

In particular embodiments, the hydrogen exiting bioreactor 2 can be monitored continuously or at discrete time point. Furthermore, adjustments means 9 can be configured to make continuous adjustments or adjustments at discrete time points if necessary.

Any means for determining the hydrogen produced by the culture can be used, however in particular embodiments; one or more gas chromatographs are used to determine H2 concentrations of the stream exiting the bioreactor 2 and optionally substrate stream 1. In one embodiment, the means for determining the H2 concentrations in the stream exiting bioreactor 2 is a Varian CP-4900 micro GC.

EXAMPLES

Materials and Methods

| Solution A | |
|---|---|
| $NH_4Ac$ | 3.083 g |
| $MgCl_2 \cdot 6H_2O$ | 0.4 g |
| $CaCl_2 \cdot 2H_2O$ | 0.294 g |
| KCl | 0.15 g |
| NaCl (optional) | 0.12 g |
| Distilled Water | Up to 1 L |

| Solution B | |
|---|---|
| Biotin | 20.0 mg |
| Folic acid | 20.0 mg |
| Pyridoxine•HCl | 10.0 mg |
| Thiamine•HCl | 50.0 mg |
| Riboflavin | 50.0 mg |
| Nicotinic acid | 50.0 mg |
| Calcium D-(*)-pantothenate | 50.0 mg |
| Vitamin B12 | 50.0 mg |
| p-Aminobenzoic acid | 50.0 mg |
| Thioctic acid | 50.0 mg |
| Distilled water | To 1 Liter |

| Solution C | |
|---|---|
| Component/0.1M solution (aq) | Quantity/ml |
| $FeCl_3$ | 10 ml |
| $CoCl_2$ | 1 ml |
| $NiCl_2$ | 0.1 ml |
| $H_3BO_3$ | 1 ml |
| $Na_2MoO_4$ | 0.1 ml |
| $ZnCl_2$ | 1 ml |
| $Na_2WO_4$ | 0.1 ml |
| Distilled water | To 1 Liter |

| Solution D | |
|---|---|
| Component | Conc. (in $H_2O$) |
| $FeSO_4$ | 0.1 mol/L |
| $CoCl_2$ | 0.05 mol/L |
| $NiCl_2$ | 0.05 mol/L |
| $Na_2MoO_4$ | 0.01 mol/L |

-continued

| | |
|---|---|
| ZnCl$_2$ | 0.01 mol/L |
| H$_3$BO$_3$ | 0.01 mol/L |

Solution E

| Media Component | Quantity |
|---|---|
| MgCl$_2$·6H$_2$O | 0.5 g |
| NaCl | 0.2 g |
| CaCl$_2$ | 0.2 g |
| NaH$_2$PO$_4$ | 2.04 g |
| NH$_4$Cl | 2.5 g |
| 85% H$_3$PO$_4$ | 0.05 ml |
| KCl | 0.15 g |
| Solution B | 10 mL |
| Solution C | 10 mL |
| Resazurin (2 mg/L stock) | 1 mL |
| FeCl$_3$ | 1 ml |
| Cysteine·HCl monohydrate | 0.5 g |
| Distilled water | To 1 liter |

Solution F

| Component | Quantity |
|---|---|
| FeCl$_3$ (0.1M solution) | 30 ml |
| CoCl$_2$ (0.1M solution) | 30 ml |
| NiCl$_2$ (0.1M solution) | 30 ml |
| Na$_2$S·9H$_2$O | 2.8 g |
| Distilled water | To 300 ml |

Solution G

| Component | Quantity |
|---|---|
| FeCl$_3$ (0.1M solution) | 10 ml |
| CoCl$_2$ (0.01M solution) | 5 ml |
| NiCl$_2$ (0.1M solution) | 5 ml |
| Na$_2$MoO$_4$ (0.01M solution) | 5 ml |
| Na$_2$WO$_4$ (0.01M solution) | 5 ml |
| ZnCl$_2$ (0.01M solution) | 5 ml |
| Distilled water | To 1 Liter |

Solution H

| Component | Mol/L H2O |
|---|---|
| FeCl$_2$ | 0.01 |
| CoCl$_2$ | 0.0002 |
| NiCl$_2$ | 0.005 |
| H$_3$BO$_3$ | 0.0002 |
| Na2WO4 | 0.0002 |
| Na$_2$SeO$_3$ | 0.0002 |
| Na$_2$MoO$_4$ | 0.0002 |
| ZnCl$_2$ | 0.0005 |
| MnCl2 | 0.0002 |
| Nitriloactetic acid | 0.003 |

Solution J

| Component | Mol/L H2O |
|---|---|
| FeCl$_3$ | 0.1 |
| CoCl$_2$ | 0.05 |
| NiCl$_2$ | 0.05 |
| H$_3$BO$_3$ | 0.01 |
| Na$_2$SeO$_3$ | 0.01 |
| Na$_2$MoO$_4$ | 0.01 |
| ZnCl$_2$ | 0.01 |
| MnCl2 | 0.01 |

Solution K

| Component | Pr L/stock |
|---|---|
| Thiamine (B1) | 84.3 mg |
| Pantothenic acid (B5) | 59.6 mg |
| Biotin (B7) | 61.1 mg |
| Distilled water | Up to 1 L |

Solution L

| Component | Pr L/stock |
|---|---|
| Thiamine (B1) | 84.3 mg |
| Pantothenic acid (B5) | 59.6 mg |
| Lipoic acid | 51.6 mg |
| Biotin (B7) | 61.1 mg |
| Distilled water | Up to 1 L |

Preparation of Na$_2$S$_x$

A 500 ml flask was charged with Na$_2$S (93.7 g, 0.39 mol) and 200 ml H$_2$O. The solution was stirred until the salt had dissolved and sulfur (25 g, 0.1 mol) was added under constant N$_2$ flow. After 2 hours stirring at room temperature, the "Na$_2$S$_x$" solution (approx 4M with respect to [Na] and approx 5M with respect to sulfur), now a clear reddish brown liquid, was transferred into N$_2$ purged serum bottles, wrapped in aluminum foil.

Preparation of Cr (II) Solution

A 1 L three necked flask was fitted with a gas tight inlet and outlet to allow working under inert gas and subsequent transfer of the desired product into a suitable storage flask. The flask was charged with CrCl$_3$.6H$_2$O (40 g, 0.15 mol), zinc granules [20 mesh] (18.3 g, 0.28 mol), mercury (13.55 g, 1 mL, 0.0676 mol) and 500 ml of distilled water. Following flushing with N$_2$ for one hour, the mixture was warmed to about 80° C. to initiate the reaction. Following two hours of stirring under a constant N$_2$ flow, the mixture was cooled to room temperature and continuously stirred for another 48 hours by which time the reaction mixture had turned to a deep blue solution. The solution was transferred into N$_2$ purged serum bottles and stored in the fridge for future use.

Bacteria:

The *Clostridium autoethanogenum* used is that deposited at the German Resource Centre for Biological Material (DSMZ) and allocated the accession number 19630.

Sampling and Analytical Procedures

Media samples were taken from the CSTR reactor at intervals over the course of each fermentation. Each time the media was sampled care was taken to ensure that no gas was allowed to enter into or escape from the reactor.

HPLC:

HPLC System Agilent 1100 Series. Mobile Phase: 0.0025N Sulfuric Acid. Flow and pressure: 0.800 mL/min. Column: Alltech IOA; Catalog #9648, 150×6.5 mm, particle size 5 μm. Temperature of column: 60° C. Detector: Refractive Index. Temperature of detector: 45° C.

Method for Sample Preparation:

400 μL of sample and 50 μL of 0.15M ZnSO$_4$ and 50 μL of 0.15M Ba(OH)$_2$ are loaded into an Eppendorf tube. The tubes are centrifuged for 10 min. at 12,000 rpm, 4° C. 200 μL of the supernatant are transferred into an HPLC vial, and 5 μL are injected into the HPLC instrument.

Headspace Analysis:

Measurements were carried out on a Varian CP-4900 micro GC with two installed channels. Channel 1 was a 10 m Molsieve column running at 70° C., 200 kPa argon and a backflush time of 4.2 s, while channel 2 was a 10 m PPQ column running at 90° C., 150 kPa helium and no backflush. The injector temperature for both channels was 70° C. Runtimes were set to 120 s, but all peaks of interest would usually elute before 100 s.

Cell Density:

Cell density was determined by counting bacterial cells in a defined aliquot of fermentation broth. Alternatively, the absorbance of the samples was measured at 600 nm (spectrophotometer) and the dry mass determined via calculation according to published procedures.

Example 1

Batch Fermentation

Approximately 1400 mL of solution A was transferred into a 1.5 L fermenter and sparged with nitrogen. Resazurin (1.5 mL of a 2 g/L solution) and $H_3PO_4$ (85% solution, 2 mL) was added and the pH adjusted to 5.3 using concentrated $NH_4OH$ (aq). Chromium(II)chloride was added until the ORP of the solution decreased to approximately −150 mV. Sodium polysulfide (4.2 mL of a 4.3M solution) was added, the solution sparged with N2, then solution D (1.5 mL), solution B (15 mL) and $Na_2WO_3$ (1.5 mL of a 0.01M solution) were added. Solution F (15 mL) was added, the pH was adjusted to 5.5 and the solution sparged with N2 before switching to CO containing gas (50% CO; 50% N2) at 40 mL/min. The reactor was then inoculated with 150 ml of a *Clostridium autoethanogenum* culture. The bioreactor was maintained at 37° C. and stirred at 300 rpm. During the growth phase, the agitation was increased to stepwise to 800 rpm.

Figure 3:
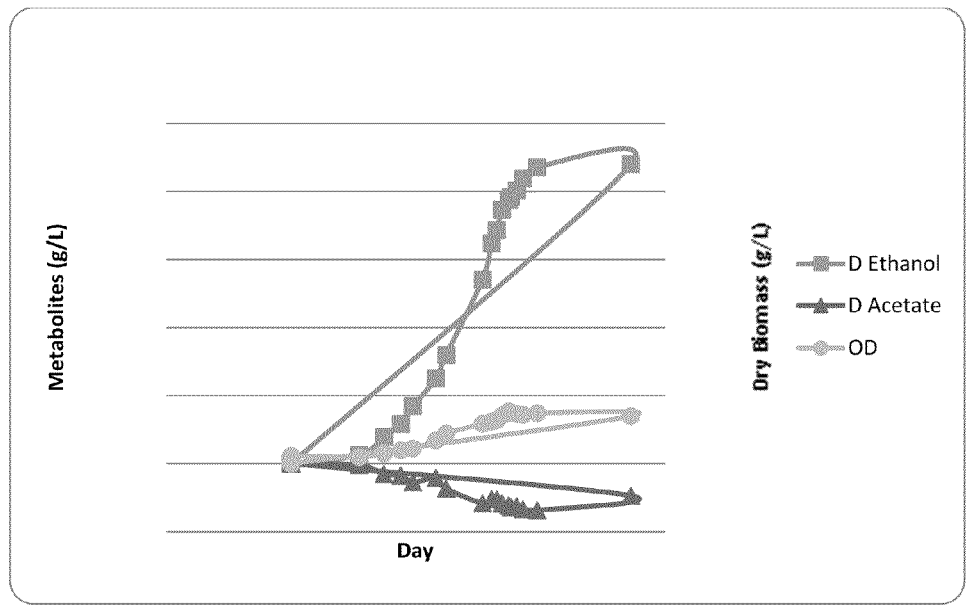
FIG. 3: shows microbial growth and metabolite production as described in example 1.
Figure 4:
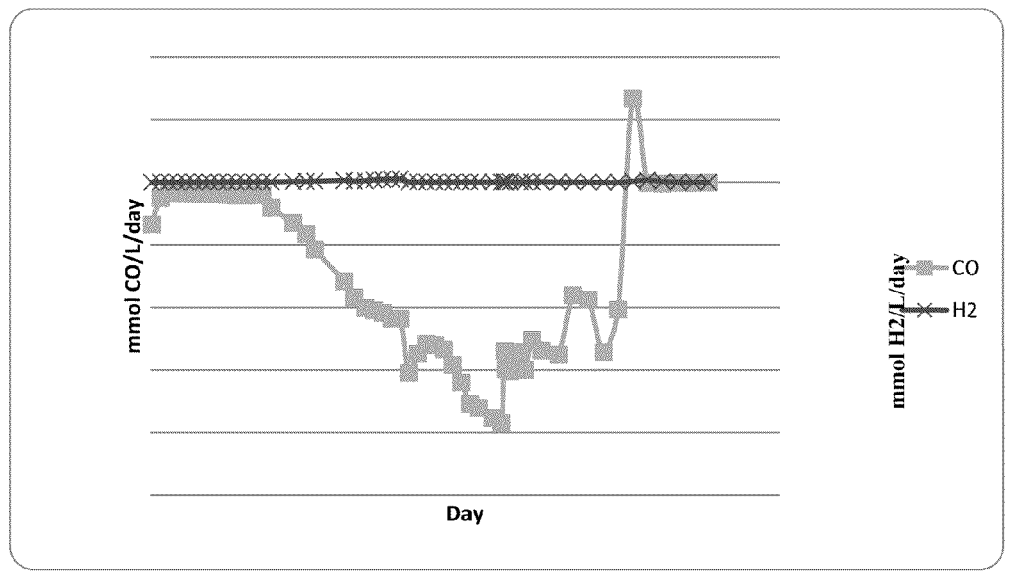
FIG. 4: shows CO consumption and H2 production as described in example 1.

Metabolite and microbial growth can be seen in FIG. 3. During the growth phase (initiated at approx day 0.5), substrate supply was increased by increasing agitation and/or gas flow rate. In FIG. 3, it can be seen that exponential growth occurs between day 0.5 and 1.2. The substrate supply was increased in accordance with microbial growth to maintain hydrogen production by the culture at a level between approx 1-2.5 mol %. Following day 1.2, the CO supply was increased, however H2 production dropped substantially, indicating a slight oversupply of substrate. H2 production and CO consumption can be seen in FIG. 4. While the culture continues to grow and produce metabolites after day 1.2, the growth rate substantially slows and is no longer exponential. By controlling substrate supply, such that H2 is produced, ethanol is produced without concomitant acid production.

Table 1 shows that by maintaining substrate supply such that hydrogen is produced by the culture, specific CO uptake can be maintained at a high level of at least 0.6 mmol/g/min and up to approx 1.2 mmol/g/min.

TABLE 1

H2 production, as a function of CO consumed and specific CO uptake during the exponential growth period of Example 1.

| Day | $H2_{produced}/CO_{consumed}$ (mol %) | Specific CO uptake mmol/g biomass/min |
|---|---|---|
| 0.53 | 1.9 | 0.3 |
| 0.58 | 1.2 | 0.6 |
| 0.68 | 1.8 | 0.8 |
| 0.74 | 1.7 | 0.8 |
| 0.78 | 1.6 | 1.0 |
| 0.92 | 1.8 | 1.2 |
| 0.97 | 0.93 | 1.2 |
| 1.02 | 1.2 | 1.3 |
| 1.07 | 1.9 | 1.3 |
| 1.11 | 2.3 | 1.1 |
| 1.15 | 2.4 | 1.0 |
| 1.19 | 2.4 | 0.9 |

Example 2

Media was prepared at pH 5.5 as follows. All ingredients in solution E with the exception of Cysteine-HCl were mixed in 400 ml distilled water. This solution was made anaerobic by heating to boiling and allowing it to cool to room temperature under a constant flow of 95% CO, 5% CO2 gas. Once cool, the Cysteine-HCl was added and the pH of the solution adjusted to 5.5 before making the volume up to 1000 ml; anaerobicity was maintained throughout the experiments.

A 1 L bioreactor was charged with 400 ml Solution E media, prepared as described above under a constant flow of N2. The gas was switched to CO containing gas (50% CO; 50% N2) at atmospheric pressure prior to inoculation with 400 ml of a *Clostridium autoethanogenum* culture. The bioreactor was maintained at 37° C. stirred at 400 rpm at the start of the culture. During the growth phase, the agitation was increased to 400 rpm. The pH was maintained at 5.5 before allowing it to drop to pH 5.3. Following the initial growth phase, the culture was switched to continuous operation by adding fresh media at a dilution rate of approximately 1 reactor volume per day. The fresh media was prepared in accordance with the above, but contained additional nickel (approx 0.5 mL/L of a 0.1M solution).

Figure 5:
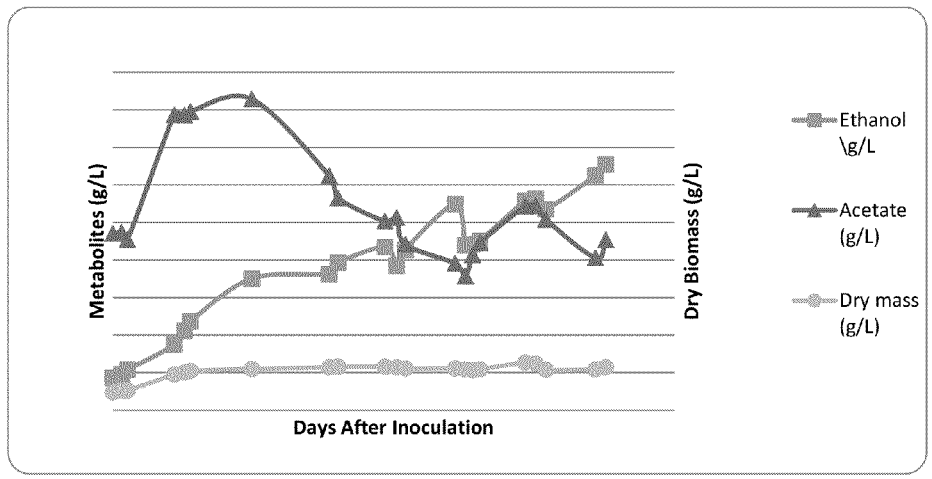
FIG. 5: shows microbial growth and metabolite production as described in example 2.
Figure 6:
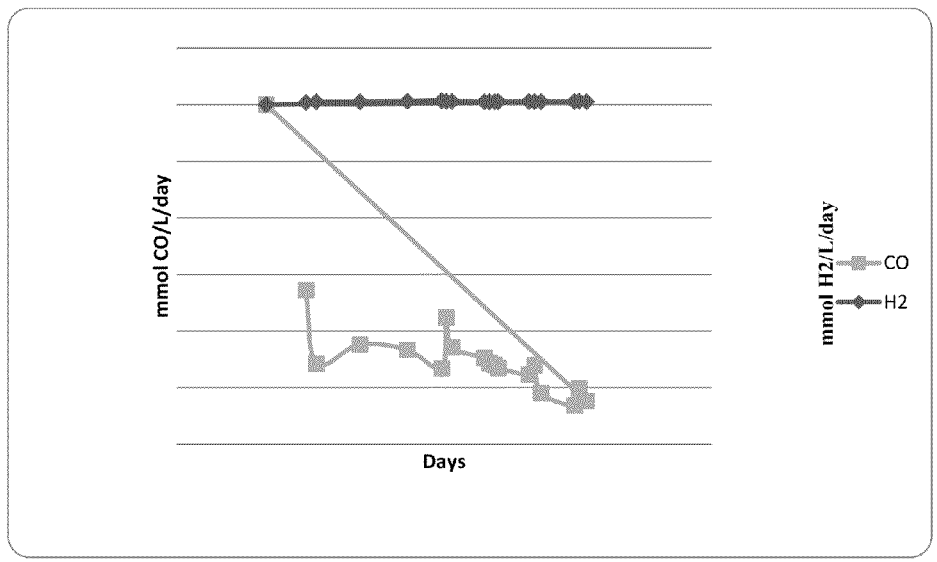
FIG. 6: shows CO consumption and H2 production as described in example 2.

Following the initial growth phase, biomass was maintained at a constant level by supplying substrate such that H2 was continuously produced (see FIGS. 5 and 6). During this time, substrate supply was increased such that specific uptake increased to approx 0.8-0.9 mmol/g/min (see Table 2). Ethanol productivity increased to approx 9-10 g/L/day, while acetate productivity remained at 6-8 g/L/day.

TABLE 2

H2 production, as a function of CO consumed and specific CO uptake during the exponential growth period of Example 2.

| Day | $H2_{produced}/CO_{consumed}$ (mol %) | Specific CO uptake mmol/g biomass/min |
|---|---|---|
| 0.90 | 1.1 | 0.64 |
| 1.13 | 1.1 | 0.81 |
| 2.10 | 1.2 | 0.70 |
| 3.17 | 1.3 | 0.70 |
| 3.94 | 1.5 | 0.75 |
| 4.04 | 1.5 | 0.61 |
| 4.17 | 1.3 | 0.72 |
| 4.90 | 1.1 | 0.74 |
| 5.01 | 1.1 | 0.78 |
| 5.13 | 1.1 | 0.80 |
| 5.21 | 1.1 | 0.79 |
| 5.90 | 1.1 | 0.70 |
| 6.02 | 1.1 | 0.69 |
| 6.17 | 1.0 | 0.88 |
| 6.92 | 1.0 | 0.90 |
| 7.02 | 1.2 | 0.81 |
| 7.19 | 1.0 | 0.86 |

Example 3

A 1 L bioreactor was charged with 200 ml Solution E media prepared as described above, under a constant flow of N2. The gas was switched to CO containing gas (50% CO; 20% CO2; 3% H2; 27% N2) at atmospheric pressure prior to inoculation with 800 ml of a *Clostridium autoethanogenum* culture. The bioreactor was maintained at 37° C. stirred at 200 rpm at the start of the culture. During the growth phase, the agitation was increased to 400 rpm. The pH was adjusted to 5.5 and maintained by automatic addition of 5 M NaOH. Following an initial growth period, the culture was switched to continuous operation by adding fresh media at a dilution rate of approximately 1 reactor volume per day.

Figure 7:
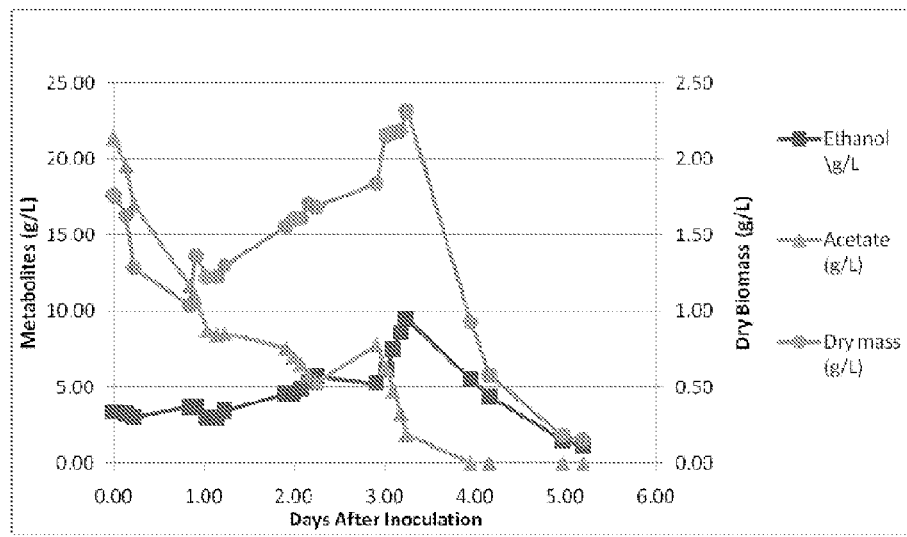
FIG. 7: shows microbial growth and metabolite production as described in example 3.
Figure 8:
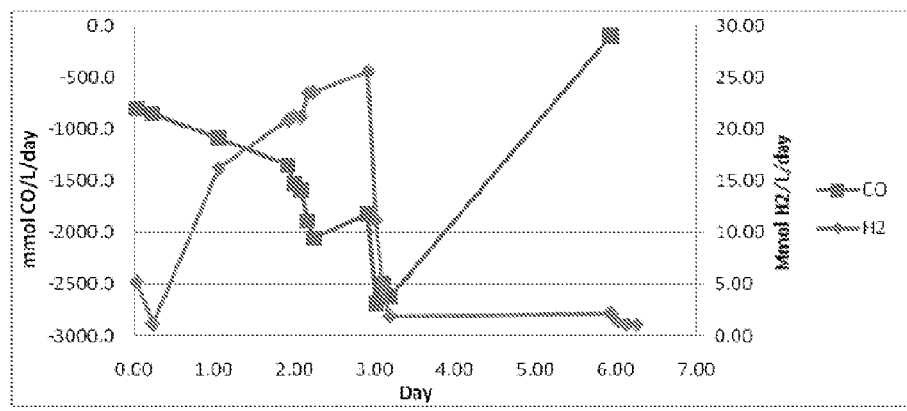
FIG. 8: shows CO consumption and H2 production as described in example 3.

Microbial growth, metabolite production and gas consumption/production data can be seen in FIGS. 7 and 8. Substrate supply was increased over time by increasing agitation and gas flow. At day 1.9, agitation was increased 100 rpm every two hours for 8 hours. During that time, CO consumption increased and H2 production increased slightly, indicating CO being supplied at or approaching an optimum level. During this time, specific CO uptake increases from 0.6 mmol/g/min up to 0.9 mmol/g/min.

On day 2.9, gas flow was increased stepwise (10 mL/min increments every 2 hours). Following gas supply increases, CO consumption increased, but H2 production dropped. FIG. 6 shows growth slows during this period leading to a rapid drop in biomass.

Example 4

Approximately 1400 mL of solution A was transferred into a 1.5 L fermenter and sparged with nitrogen. Resazurin (1.5 mL of a 2 g/L solution) and $H_3PO_4$ (85% solution, 2 mL) was added and the pH adjusted to 5.3 using concentrated $NH_4OH$ (aq). Chromium(II)chloride was added until the ORP of the solution decreased to approximately −150 mV. Sodium polysulfide (4.2 mL of a 4.3M solution) was added, the solution sparged with N2, then solution B (15 mL), solution G (1.5 mL) and $Na_2WO_3$ (1.5 mL of a 0.01M solution) were added. Solution F (15 mL) was added, the pH was adjusted to 5.5 and the solution sparged with N2 before switching to CO containing gas (50% CO; 50% N2) at 40 mL/min. The reactor was then inoculated with 150 ml of a *Clostridium autoethanogenum* culture. The bioreactor was maintained at 37° C. and stirred at 300 rpm. During the growth phase, the agitation was increased to stepwise to 800 rpm.

Figure 9:
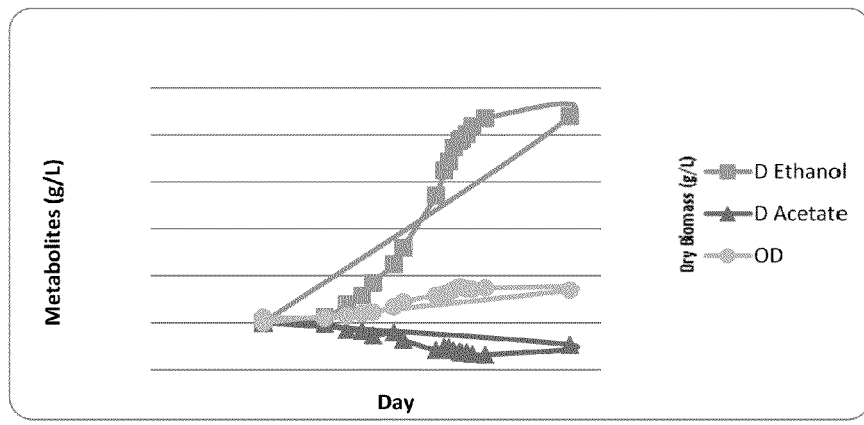
FIG. 9: shows microbial growth and metabolite production as described in example 4.
Figure 10:
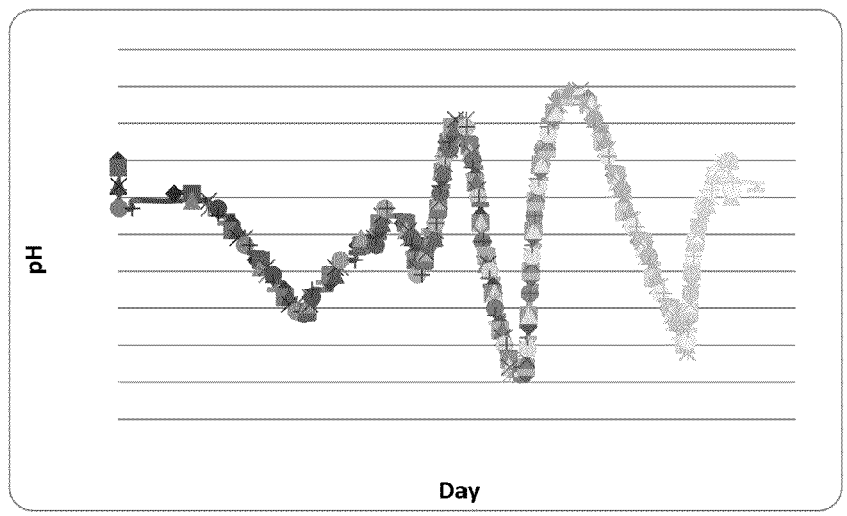
FIG. 10: shows pH changes during fermentation as described in example 4.

Metabolite and microbial growth can be seen in FIG. 9. During the growth phase (initiated at approx day 0.5), substrate supply was increased by increasing agitation and/or gas flow rate. In FIG. 9, it can be seen that exponential growth occurs between day 0.5 and 1.2. The substrate supply was increased in accordance with microbial growth to maintain pH of the media between approximately pH 5 and 5.6 as shown in FIG. 10. From day 0.5, the substrate availability was increased slowly by increasing agitation and/or gas flow. From day 0.5 to 1.0, the substrate was provided such that there was a net conversion of acetate to ethanol in addition to microbial growth and alcohol biosynthesis. During this time, the pH increased slowly to approximately 5.6. From day 1.0 to day 1.2, the substrate availability was substantially maintained constant. During this time, the microbial culture continued to grow substantially exponentially. There was a net production of acetate and the pH dropped to approximately 4.9. Following day 1.2, the CO supply was increased; however pH rose rapidly from 4.9 to approximately 5.6, indicating net acetate consumption associated with an oversupply of substrate. While the culture continues to grow and produce metabolites after day 1.2, the growth rate substantially slows and is no longer exponential.

Table 1 shows that by maintaining substrate supply such that pH is maintained within a desirable range, specific CO uptake can be maintained at a high level of at least 0.6 mmol/g/min and up to approx 1.2 mmol/g/min.

TABLE 1 pH and specific CO uptake during the exponential growth period of Example 1.

| Day | pH | Specific CO uptake mmol/g biomass/min |
|---|---|---|
| 0.53 | 5.1 | 0.3 |
| 0.58 | 5.2 | 0.6 |
| 0.68 | 5.2 | 0.8 |
| 0.74 | 5.3 | 0.8 |
| 0.78 | 5.3 | 1.0 |
| 0.92 | 5.3 | 1.2 |
| 0.97 | 5.5 | 1.2 |
| 1.02 | 5.6 | 1.3 |
| 1.07 | 5.3 | 1.3 |
| 1.11 | 5.1 | 1.1 |
| 1.15 | 5.0 | 1.0 |
| 1.19 | 4.9 | 0.9 |

Example 5A

Continuous Fermentation in CSTR

Media was prepared as follows: 100 ml of Solution A was added to 1.7 L of water. 85% $H_3PO_4$ (30 mM) was added and the media solution was sterilised by autoclaving for 30 minutes at 121° C., or by filter sterilisation prior to use. The media solution was aseptically and anaerobically transferred into a 3 L CSTR vessel, and continuously sparged with $N_2$.

pH was increased with the addition of ammonium hydroxide. 20 ml of trace metal solution H, then 2 ml of Glacial Acetic acid and 20 ml of Solution B were added. CrII was added until the solution went clear. Prior to inoculation, the gas was switched to 2% h2, 33% N2, 45% CO and 22% CO2. An actively growing *Clostridium autoethanogenum* culture was inoculated into the CSTR at a level of approximately 12% (v/v). During this experiment, Na2S (0.2M) solution was added at a rate of approx 0.4 ml/hour.

The microbial culture was allowed to grow in batch mode for approximately 1 day. At day 1, the fermentation was switched to continuous operation wherein fresh media was provided at a dilution rate of approximately 1.5 to 1.8 reactor volumes per day. Substrate supply was increased automatically in response to the requirements of the microbial culture in accordance with the invention (described below).

Figure 11:
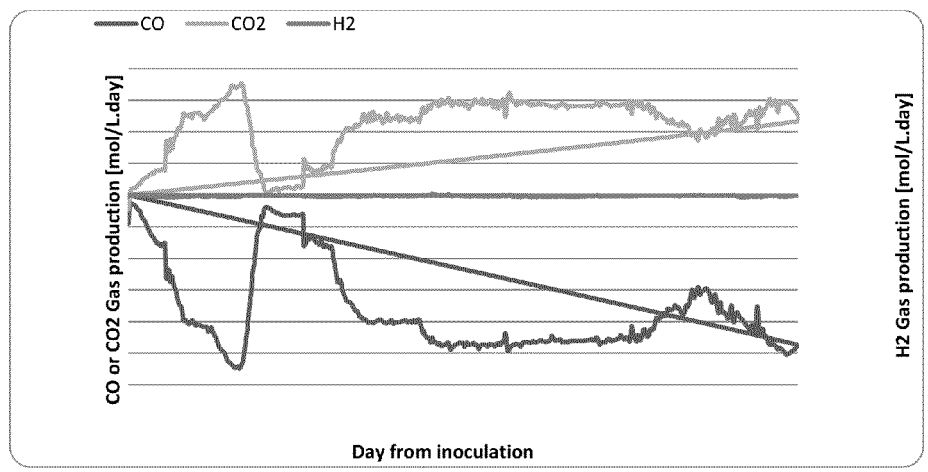
FIG. 11: shows gas consumption/production as described in example 5A.
Figure 12:
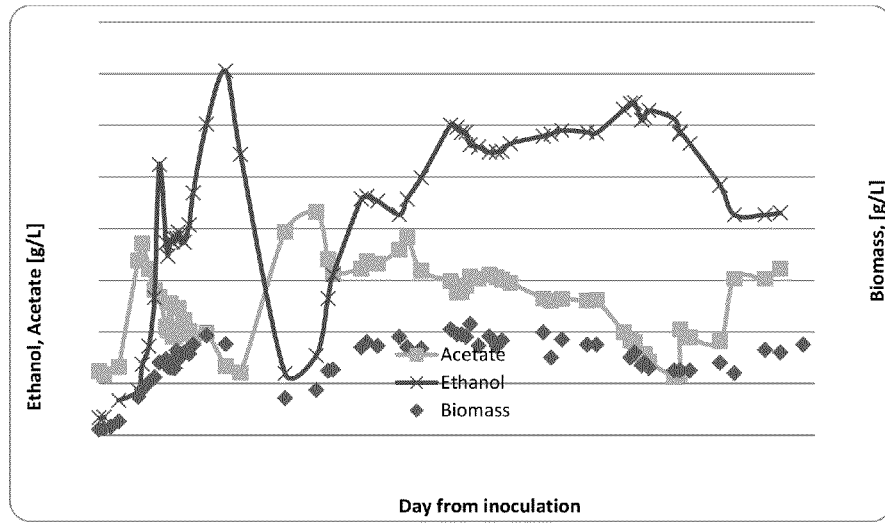
FIG. 12: shows microbial growth and metabolite production as described in example 5A.

Results of the fermentation are shown in FIGS. 11-12. The substrate supply rate and agitation rate were increased or decreased automatically over the time course of the fermentation in response to changes in pH. Initially, in the batch growth phase, the pH was automatically maintained at approximately pH 5.5 by increasing the substrate supply. On turning the fermentation onto continuous operation, the substrate was provided such that a substantially constant rate of pH change was achieved. If the rate of change increased, the substrate supply was automatically increased to bring the pH rate of change back to a predetermined value. Conversely, if the rate of change decreased (or the pH started to increase), the substrate supply was decreased. The rate of pH change was approximately three pH units per day. Sustainable continuous operation resulted in a stable biomass of approximately 3 g/L, substantially stable acetate concentration of approximately 5 g/L and substantially stable ethanol concentration of at least 10 g/L. This equates to a specific productivity of acetate of approximately 2 g/g biomass/day and approx 4 g/g biomass/day ethanol.

Example 5B

Continuous Fermentation in CSTR

All liquid fermentation broth from example 5A was directed into a 3 L CSTR fitted with a hydrophilic Xampler cell recycle membrane from GE Healthcare, pore size: 0.1 NMWC, fibre internal diameter: 1 mm, membrane area: 0.011 m2. The fermenter was operated such that a constant volume was maintained and continuously provided with a substrate stream comprising 2% H2, 33% N2, 45% CO and 22% CO2. The cell recycle loop was operated such that approximately 70% of the microbial biomass was retained in the fermenter at each pass.

Figure 13:
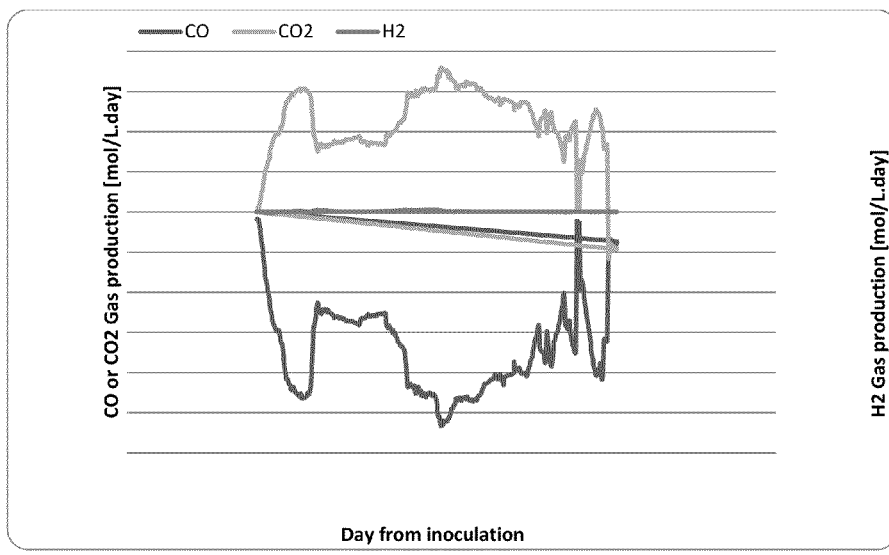
FIG. 13: shows gas consumption/production as described in example 5B.
Figure 14:
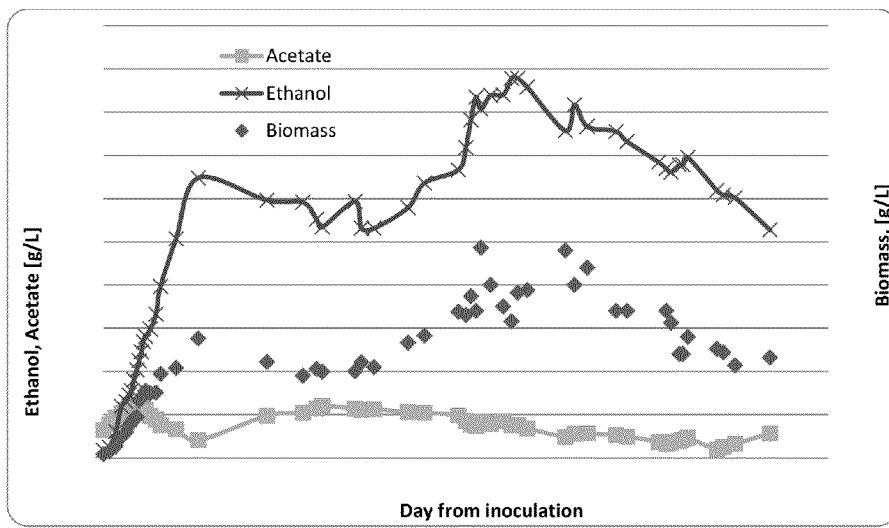
FIG. 14: shows microbial growth and metabolite production as described in example 5B.

Substrate gas was automatically provided such that pH was substantially maintained at approximately 5.3. During fermentation, if the pH started to increase, the substrate supply was decreased. Conversely, if the pH started to decrease, the substrate supply was increased. Results of the fermentation are shown in FIGS. 13-14. As the microbial density increased as a result of cell retention and/or microbial growth, the substrate supply automatically increases to maintain a substantially constant pH. Maintaining a constant pH slightly below the pH of the incoming fermentation broth results in a net conversion of acetate into ethanol. During fermentation, no acetate was produced, so the net level in the fermenter decreased to less than 5 g/L, while the ethanol accumulated to at least 40 g/L. Operating the fermenter in this manner resulted in a constant production of H2. Between day 6 and 7, the amount of H2 produced by the culture was approximately 1 mol %.

Example 6

Continuous Fermentation in CSTR

A 2 L CSTR was set up under the following conditions: Media was prepared as follows: 85% $H_3PO_4$ (30 mM) was added to 1.5 L of solution A. The pH of the media was adjusted to 5.3 by the addition of NH4OH. The media solution was sterilised by autoclaving for 30 minutes at 121° C., or by filter sterilisation prior to use. Resazurin was added as a redox indicator. The media solution was aseptically and anaerobically transferred into a 1.5 L CSTR vessel, and continuously sparged with $N_2$. Once transferred to the fermentation vessel, the reduction state and pH of the transferred media could be measured directly via probes. The media was heated to 37° C. and stirred at 300 rpm, then trace metal solution J (1.5 mL) and nitriloactetic acid (0.15M solution, 0.3 ml), then Na2WO3 (1.5 mL of a 0.01M solution) then Solution K (15 mL) were added. Prior to inoculation, the gas was switched to 50% N2 and 50% CO. An actively growing *Clostridium autoethanogenum* culture was inoculated into the CSTR at a level of approximately 12% (v/v). During this experiment, Na2S (0.2M) solution was added at a rate of approx 0.3 ml/hour.

Figure 15:
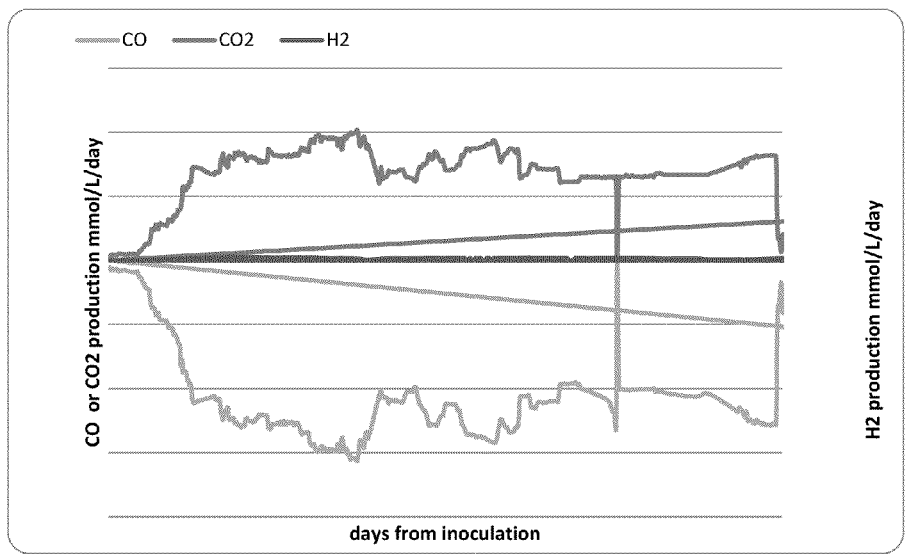
FIG. 15: shows gas consumption/production as described in example 6.
Figure 16:
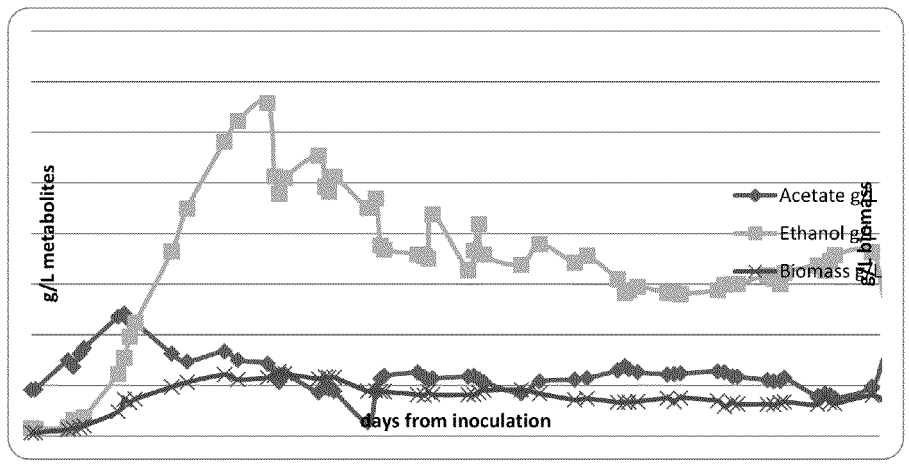
FIG. 16: shows microbial growth and metabolite production as described in example 6.

The microbial culture was allowed to grow in batch mode for approximately 1 day. At day 1, the fermentation was switched to continuous operation wherein fresh media was provided. Substrate supply was increased in response to the requirements of the microbial culture. Results of the fermentation are shown in FIGS. 15-16. Following an initial period of stabilisation, the fermentation was operated such that the biomass stabilised at approximately 3 g/L, while acetate was maintained at a concentration of approximately 5 g/L and ethanol was maintained at a concentration of 15-20 g/L. At a dilution rate of approximately 1.5, the specific acetate productivity is approximately 1.2 g/g biomass/day, while the ethanol productivity ranges from approximately 4-6 g/g biomass/day.

H2 was also produced throughout the fermentation at levels exceeding 1 mol %.

The invention has been described herein with reference to certain preferred embodiments, in order to enable the reader to practice the invention without undue experimentation. Those skilled in the art will appreciate that the invention is susceptible to variations and modifications other than those specifically described. It is to be understood that the invention includes all such variations and modifications. Furthermore, titles, heading, or the like are provided to enhance the reader's comprehension of this document, and should not be read as limiting the scope of the present invention. The entire disclosures of all applications, patents and publications cited above and below, if any, are herein incorporated by reference.

The reference to any prior art in this specification is not, and should not be taken as, an acknowledgement or any form of suggestion that that prior art forms part of the common general knowledge in the field of endeavour in any country in the world.

Throughout this specification and any claims which follow, unless the context requires otherwise, the words "comprise", "comprising" and the like, are to be construed in an inclusive sense as opposed to an exclusive sense, that is to say, in the sense of "including, but not limited to".

What we claim is:

1. A method for optimising ethanol production in a continuous fermentation process, the method comprising;
    a) providing a gaseous substrate comprising CO to a bioreactor comprising a culture of at least one carboxydotrophic acetogenic microorganism in a fermentation broth;
    b) fermenting the substrate to produce ethanol and acetate;
    c) adjusting the substrate supply to the fermentation broth such that the microorganism produces hydrogen;
    d) determining an optimum hydrogen production;
    e) monitoring the hydrogen production; and
    f) adjusting the substrate supply in response to a change in the hydrogen production such that ethanol production is optimized.

2. The method of claim 1 where the hydrogen produced is at least 0.5 mol % of the CO substrate consumed.

3. The method of claim 1 where the hydrogen produced is maintained in the range of about 0.5 mol % to about 2.0 mol % of the CO substrate consumed.

4. The method of claim 1 where the hydrogen produced is at least 1.0 mol % of the CO substrate consumed.

5. The method of claim 1 wherein the substrate comprises at least 15% to 95% CO by volume.

6. The method of claim 1 wherein the carboxydotrophic acetogenic micro-organism is selected from the group consisting of *Clostridium, Moorella, Pyrococcus, Eubacterium, Desulfobacterium, Carboxydothermus, Acetogenium, Acetobacterium, Acetoanaerobium, Butyribacterium* and *Peptostreptococcus*.

7. The method of claim 6 wherein the carboxydotrophic acetogenic micro-organism is selected from the group consisting of *Clostridium autoethanogenum, Clostridium ljungdahlii, Clostridium ragsdalei* and *Clostridium carboxydivorans*.

* * * * *